US008021341B2

(12) United States Patent
Lampropoulos et al.

(10) Patent No.: US 8,021,341 B2
(45) Date of Patent: *Sep. 20, 2011

(54) SELF-SUTURING ANCHOR DEVICE

(75) Inventors: Fred P. Lampropoulos, Salt Lake City, UT (US); Brian Stevens, Pleasant Grove, UT (US)

(73) Assignee: Merit Medical Systems, Inc., South Jordan, UT (US)

( * ) Notice: Subject to any disclaimer, the term of this patent is extended or adjusted under 35 U.S.C. 154(b) by 254 days.

This patent is subject to a terminal disclaimer.

(21) Appl. No.: 12/436,012

(22) Filed: May 5, 2009

(65) Prior Publication Data

US 2009/0281503 A1 Nov. 12, 2009

Related U.S. Application Data

(60) Division of application No. 11/532,056, filed on Sep. 14, 2006, now Pat. No. 7,544,187, which is a continuation-in-part of application No. 11/202,484, filed on Aug. 11, 2005, now Pat. No. 7,540,857, which is a continuation-in-part of application No. 11/198,666, filed on Aug. 5, 2005, now Pat. No. 7,470,256, which is a continuation of application No. 11/082,170, filed on Mar. 16, 2005, now Pat. No. 7,520,869.

(60) Provisional application No. 60/623,502, filed on Oct. 29, 2004, provisional application No. 60/627,485, filed on Nov. 12, 2004.

(51) Int. Cl.
*A61M 5/32* (2006.01)
(52) U.S. Cl. ........................................................ 604/180
(58) Field of Classification Search .................. 604/116, 604/117, 174–180; 606/139–153
See application file for complete search history.

(56) References Cited

U.S. PATENT DOCUMENTS 2,669,231 A 2/1954 Fisher
3,406,685 A 10/1968 May
(Continued)

FOREIGN PATENT DOCUMENTS

WO WO 2006/050080 5/2006
(Continued)

OTHER PUBLICATIONS

Notification of Transmittal of the International Search Report and the Written Opinion of the International Searching Authority issued Jun. 14, 2006 in International Application No. PCT/US2005/038910.

(Continued)

*Primary Examiner* — Nicholas D Lucchesi
*Assistant Examiner* — Nathan R Price
(74) *Attorney, Agent, or Firm* — Stoel Rives LLP

(57) ABSTRACT

A catheter anchor device for use with a catheter includes an adhesive layer configured to be secured to the skin of the patient proximate the catheter insertion site, a stationary base secured to the adhesive layer, a rotatable ring coupled to the stationary base and circumscribing the stationary base such that the rotatable outer ring can be rotated by the user relative to the stationary base, a first suture including a loop portion and first and second ends, the loop portion looping around a catheter when the anchor device is in place relative to the catheter insertion site, and a pull handle including first and second separable pull tabs, the pull handle being coupled to the first and second ends of the first suture, the pull handle being configured such that actuation of the pull handle actuates first suture to secure the catheter relative to the rotatable ring.

17 Claims, 16 Drawing Sheets

U.S. PATENT DOCUMENTS

| | | | |
|---|---|---|---|
| 3,858,740 | A | 1/1975 | Lestaevel |
| 4,221,215 | A | 9/1980 | Mandelbaum |
| 4,296,949 | A | 10/1981 | Muetterties et al. |
| 4,372,073 | A | 2/1983 | Goldman |
| 4,445,893 | A | 5/1984 | Bodicky |
| 4,717,385 | A | 1/1988 | Cameron et al. |
| 4,735,442 | A | 4/1988 | Burli |
| 4,869,719 | A | 9/1989 | Hogan |
| 4,874,380 | A | 10/1989 | Hesketh |
| 5,129,891 | A | 7/1992 | Young |
| 5,137,519 | A | 8/1992 | Littrell et al. |
| 5,224,935 | A | 7/1993 | Hollands |
| 5,312,337 | A | 5/1994 | Flaherty et al. |
| 5,416,952 | A | 5/1995 | Dodge |
| 5,599,328 | A | 2/1997 | Stevens |
| 5,672,158 | A | 9/1997 | Okada et al. |
| 5,674,201 | A | 10/1997 | Steinman |
| 5,681,288 | A | 10/1997 | Schlitt |
| 5,897,497 | A | 4/1999 | Fernandez |
| 5,911,229 | A | 6/1999 | Chodorow |
| 5,944,697 | A | 8/1999 | Biche |
| 6,138,866 | A | 10/2000 | Lambelet, Jr. et al. |
| 6,554,297 | B2 | 4/2003 | Phillips et al. |
| 7,470,256 | B2 | 12/2008 | Lampropoulos et al. |
| 7,520,869 | B2 | 4/2009 | Lampropoulos et al. |
| 7,540,857 | B2 | 6/2009 | Backman et al. |
| 7,544,187 | B2 | 6/2009 | Lampropoulos et al. |
| 7,547,296 | B2 | 6/2009 | Lampropoulos et al. |
| 2001/0037119 | A1 | 11/2001 | Schmieding |
| 2002/0002324 | A1 | 1/2002 | McManus |
| 2002/0072713 | A1 | 6/2002 | Almond et al. |
| 2003/0229313 | A1 | 12/2003 | Bierman |
| 2006/0095008 | A1 | 5/2006 | Lampropoulos et al. |
| 2006/0095009 | A1 | 5/2006 | Lampropoulos et al. |

FOREIGN PATENT DOCUMENTS

| | | |
|---|---|---|
| WO | WO 2008/033766 | 3/2008 |

OTHER PUBLICATIONS

Supplementary European Search Report issued Aug. 20, 2007 in co-pending European Application No. 05824175.3.
Notification of Transmittal of the International Search Report and the Written Opinion of the International Searching Authority issued Apr. 10, 2008 in International Application No. PCT/US2007/078028.
Office Action issued Mar. 18, 2008 in co-pending U.S. Appl. No. 11/021,513.
Interview Summary issued Jun. 2, 2008 in co-pending U.S. Appl. No. 11/021,513.
Amendment and Response filed Jun. 18, 2008 in co-pending U.S. Appl. No. 11/021,513.
Final Office Action issued Mar. 18, 2009 in co-pending U.S. Appl. No. 11/021,513.
Response and Request for Continued Examination filed Sep. 19, 2009 in co-pending U.S. Appl. No. 11/021,513.
Office Action issued Jan. 5, 2010 in co-pending U.S. Appl. No. 11/021,513.
Notice of Allowance issued Dec. 11, 2008 in co-pending U.S. Appl. No. 11/082,170, now issued as US Patent No. 7,520,869.
Request for Continued Examination filed Nov. 12, 2008 in co-pending U.S. Appl. No. 11/082,170, now issued as US Patent No. 7,520,869.
Notice of Allowance issued Aug. 11, 2008 in co-pending U.S. Appl. No. 11/082,170, now issued as US Patent No. 7,520,869.
Response to Restriction Requirement filed May 21, 2008 in co-pending U.S. Appl. No. 11/082,170, now issued as US Patent No. 7,520,869.
Office Action issued Mar. 21, 2008 in co-pending U.S. Appl. No. 11/082,170, now issued as US Patent No. 7,520,869.
Supplemental Notice of Allowability issued Sep. 16, 2008 in co-pending U.S. Appl. No. 11/198,666, now issued as US Patent No. 7,470,256.
Notice of Allowance issued Aug. 21, 2008 in co-pending U.S. Appl. No. 11/198,666, now issued as US Patent No. 7,470,256.
Examiner-Initiated Interview Summary issued Jul. 17, 2008 in co-pending U.S. Appl. No. 11/198,666, now issued as US Patent No. 7,470,256.
Supplemental Notice of Allowability issued Feb. 4, 2009 in co-pending U.S. Appl. No. 11/202,484, now issued as US Patent No. 7,540,857.
Notice of Allowance issued Jan. 27, 2009 in co-pending U.S. Appl. No. 11/202,484, now issued as US Patent No. 7,540,857.
Preliminary Amendment filed Jan. 26, 2009 in co-pending U.S. Appl. No. 11/202,484, now issued as US Patent No. 7,540,857.
Statement of Substance of Interview filed Jan. 16, 2009 in co-pending U.S. Appl. No. 11/202,484, now issued as US Patent No. 7,540,857.
Amendment and Response to Office Action filed Dec. 19, 2008 in co-pending U.S. Appl. No. 11/202,484, now issued as US Patent No. 7,540,857.
Interview Summary issued Dec. 15, 2008 in co-pending U.S. Appl. No. 11/202,484, now issued as US Patent No. 7,540,857.
Office Action issued Jul. 29, 2008 in co-pending U.S. Appl. No. 11/202,484, now issued as US Patent No. 7,540,857.
Notice of Allowance issued Feb. 5, 2009 in co-pending U.S. Appl. No. 11/532,056, now issued as US Patent No. 7,544,187.
Interview Summary issued Dec. 29, 2008 in co-pending U.S. Appl. No. 11/532,056, now issued as US Patent No. 7,544,187.
Amendment and Response to Office Action filed Dec. 18, 2008 in co-pending U.S. Appl. No. 11/532,056, now issued as US Patent No. 7,544,187.
Office Action issued Jul. 29, 2008 in co-pending U.S. Appl. No. 11/532,056, now issued as US Patent No. 7,544,187.
Notice of Allowance issued Feb. 6, 2009 in co-pending U.S. Appl. No. 11/535,454, now issued as US Patent No. 7,547,296.
Preliminary Amendment filed Jan. 26, 2009 in co-pending U.S. Appl. No. 11/535,454, now issued as US Patent No. 7,547,296.
Statement of Substance of Interview filed Jan. 16, 2009 in co-pending U.S. Appl. No. 11/535,454, now issued as US Patent No. 7,547,296.
Amendment and Response to Office Action filed Dec. 19, 2008 in co-pending U.S. Appl. No. 11/535,454, now issued as US Patent No. 7,547,296.
Interview Summary issued Dec. 16, 2008 in co-pending U.S. Appl. No. 11/535,454, now issued as US Patent No. 7,547,296.
Office Action issued Jul. 28, 2008 in co-pending U.S. Appl. No. 11/535,454, now issued as US Patent No. 7,547,296.
Office Action dated Jun. 24, 2010 in U.S. Appl. No. 11/021,513.

SELF-SUTURING ANCHOR DEVICE

CROSS-REFERENCE TO RELATED APPLICATIONS

This application is a divisional application of U.S. patent application Ser. No. 11/532,056 entitled "Self-Suturing Anchor Device," filed on Sep. 14, 2006; which is a continuation-in-part application of U.S. Nonprovisional patent application Ser. No. 11/202,484 entitled "Self-suturing Anchor Device," filed on Aug. 11, 2005; which is a continuation-in-part application of U.S. Nonprovisional patent application Ser. No. 11/198,666 entitled "Self-suturing Anchor Device for a Catheter," filed on Aug. 5, 2005; which claims the benefit of priority to U.S. Nonprovisional patent application Ser. No. 11/082,170 entitled "Self-suturing Anchor Device for a Catheter," filed on Mar. 16, 2005; which claims the benefit of priority to U.S. Provisional Patent Application No. 60/623,502, filed on Oct. 29, 2004, entitled "Self-suturing Anchor Device for a Catheter"; and to U.S. Provisional Patent Application No. 60/627,485, filed on Nov. 12, 2004, entitled "Self-suturing Anchor Device for a Catheter", the entire specifications of which applications are incorporated herein by reference.

BACKGROUND OF THE INVENTION

1. The Field of the Invention

Exemplary embodiments of the present invention relate to the field of catheters, and, more particularly, to a self-suturing anchor device for use with a catheter.

2. Background and Relevant Art

Catheters play an important role in the treatment and care of patients in modern medicine. In particular, catheters provide relatively unobtrusive access to remote portions of a patient's body, allowing desired procedures or treatments to be performed. A wide variety of generalized and specialized catheters have been developed and refined for particular uses. For example, angioplasty catheters have been adapted to provide a safe and effective conduit for the delivery of a stent and/or balloon to a narrowing or loading blockage in a patient's artery or vein. Drainage catheters are configured to be inserted into a cavity surrounding a patient's kidney, liver, or other organ to drain excess fluid or infection from the cavity.

In addition, a number of devices and implements have been developed for use with catheters, to facilitate their effectiveness, or to overcome inherent difficulties associated with their use. For example, catheters that are designed to remain placed in a patient for long periods of time, such as for ongoing care or treatment of the patient, present a number of difficulties. Such catheters must be secured to the patient in a manner that minimizes movement of the catheter that could harm the patient or otherwise interrupt proper functioning of the catheter.

Accordingly, one approach in the prior art has been to suture the catheter directly to the patient's skin. However, when a patient repositions himself/herself in bed, the catheter may pull at the suture site or bend the catheter. Another approach is to inflate a balloon associated with the distal end of the catheter inside the patient. However, at times an incoherent patient may attempt to withdraw or otherwise remove the catheter. This can cause injury to the catheter insertion site, or can interfere with proper operation of the catheter.

In view of these and other problems in the art, a number of devices have been developed to secure a catheter in a manner that minimizes movement of the catheter, or minimizes interference with its proper operation. Typically, such devices include an adhesive layer to be secured to the patient with a small bore for accommodating the catheter and an adhesive strip to secure the catheter relative to the adhesive layer. Devices such as these are useful because they can be employed by a practitioner to secure the desired positioning of the catheter. Such devices, however, can be undesirable due at least in part to the fact that they typically cover or otherwise obstruct the catheter insertion site. This can make it difficult to identify infections, drainage, or other complications that may occur at the catheter insertion site. Furthermore, the devices can also obstruct cleaning of the insertion site, such that the site can only be cleaned by removing the anchor devices. Additionally, conventional anchor devices typically utilize a clip, or other securement member which typically is rigid or has a high profile when utilized to secure the catheter. As a result, the securement device can be uncomfortable if pressed against the patient by a chair, bed, or other object.

BRIEF SUMMARY OF SOME EMBODIMENTS OF THE INVENTION

The present invention is directed to a catheter securement device that automatically secures the catheter without requiring the practitioner to manually suture the catheter to the self-suturing anchor device. According to one embodiment, the catheter securement device includes a center aperture defined in a rotatable ring. The catheter extends through the aperture when the catheter securement device is deployed. One or more sutures are disposed about the center aperture. As a result, when the catheter securement device is in place, the suture or sutures are located around the catheter. According to one example, the first suture is looped around the catheter and includes a knot tied therein.

The catheter securement device may be secured to the patient with an adhesive. The adhesive allows a practitioner to rapidly locate the catheter securement device on the patient near the catheter insertion location. With the catheter securement device in place, a first securement is realized by pulling on the ends of a first suture. Pulling on the ends of the sutures draws the knot in the first suture into contact with the catheter, thereby securing the catheter. A pull handle is provided to further facilitate the rapid deployment of the first knot in the first suture. According to one example, the pull handle includes two separable portions, each of which has one end of the suture secured thereto. After the first knot is secured, the separable portions may be separated and a second knot tied in the first suture.

The self-suturing anchor device has a securement mechanism that is adapted to be actuated by the user to automatically secure the catheter in a quick and efficient manner. In one embodiment, a rotatable ring is provided in connection with the self-suturing anchor device to automatically secure the catheter. At least one suture thread extends from the bottom of the rotatable ring. When a user pulls the suture in a rearward direction, a loop portion of the suture is freed from the rotatable ring and initially engages a portion of the catheter associated with the bottom of the rotatable ring. The user can then rotate the rotatable ring in one or both of a clockwise or a counterclockwise direction to deploy one or more additional suture. Rotation of the rotatable ring tensions the additional suture to automatically secure the portion of the catheter positioned centrally within the rotatable ring. Once the additional suture has been secured, the first suture can be tightened and tied to further secure the catheter.

The rotatable ring is utilized in connection with a ratchet mechanism. The ratchet mechanism allows movement of the rotatable ring in a first direction while preventing movement of the rotatable ring in the opposite direction. As a result, the rotational position of the rotatable ring is secured against movement in a rearward direction. When the user rotates the rotatable ring to deploy, secure, and/or tighten the sutures relative to the catheter, inadvertent movement of the rotatable ring does not result in loosening of the sutures. Additionally, where the tension on the sutures decreases due to factors such as the natural loosening of the fibers of the suture, the user can easily ratchet the rotatable ring an additional amount to return the sutures to a desired degree of tensioning.

The ratchet mechanism includes rotatable ratchet members. The rotatable ratchet members pivot or flex allowing for movement of the portion of the rotatable ratchet member having teeth. Additionally, in one example a ratchet member engagement spring is provided which maintains contact between the teeth of the rotatable ratchet member and teeth of the ratchet ring. The ratchet member engagement spring can flex or undergo other deformation to allow for sliding of the teeth of the rotatable ratchet member over the teeth of the ratchet ring during rotation of the rotatable ring.

In one embodiment, an O-ring is provided to maintain the position of the sutures beneath the rotatable ring. The O-ring is configured to be positioned between the rotatable outer ring and base. Maintaining the position of the sutures minimizes disruption of the sutures before deployment of the sutures. In another embodiment, the base of the anchor device comprises a single molded member. The single molded member is formed utilizing first and second mold members. The base includes an undercut. As a result, the first mold member and the second mold member are formed to provide the undercut during the molding of the base.

According to one embodiment of the present invention, a method of assembling the catheter anchor device is provided. Loading of the sutures is facilitated by mounting the base of the anchor device on a loading block. A suture-loading cylinder is positioned through the center bore of the catheter anchor device and the center aperture. The suture-loading cylinder is utilized to provide a quick and effective mechanism for forming the loop configurations of the first suture, the second suture, and the third suture and for loading the sutures in the base. According to another embodiment of the present invention, one or more components of the catheter anchor device are welded to facilitate assembly of the catheter anchor device. For example, a plurality of pins of the rotatable outer ring are configured to be welded to securement bores of the bearing members. A plurality of access bores are provided in connection with the base of the anchor device such that a welding tool can be inserted through the access bores of the catheter anchor device to weld the pins of the rotatable outer ring to the securement bores of the bearing member. These and other aspects will become more fully apparent from the following description and appended claims.

BRIEF DESCRIPTION OF THE DRAWINGS

In order to describe the manner in which the above recited and other advantages and features of the invention can be obtained, a more particular description of the invention briefly described above will be rendered by reference to specific embodiments thereof, which are illustrated in the appended drawings. Understanding that these drawings depict only typical embodiments of the invention and are not therefore to be considered to be limiting of its scope, the invention will be described and explained with additional specificity and detail through the use of the accompanying drawings in which.

DETAILED DESCRIPTION OF SOME EXAMPLE EMBODIMENTS

The present invention is directed to a catheter securement device that enables securement of a catheter without requiring the practitioner to manually suture the catheter to the self-suturing anchor device. According to one embodiment, the catheter securement device includes a center aperture defined in a rotatable ring. The catheter extends through the aperture when the catheter securement device is deployed. One or more sutures are disposed about the center aperture. As a result, when the catheter securement device is in place, the suture or sutures are located around the catheter. According to one example, the first suture is looped around the catheter and includes a knot tied therein.

The catheter securement device may be secured to the patient with an adhesive. The adhesive allows a practitioner to rapidly locate the catheter securement device on the patient near the catheter insertion location. With the catheter securement device in place, a first securement is realized by pulling on the ends of a first suture. Pulling on the ends of the sutures draws the knot in the first suture into contact with the catheter, thereby securing the catheter to the catheter securement device. A pull handle is provided to further facilitate the rapid deployment of the first knot in the first suture. The pull handle is an example of a structural implementation of a means for tensioning a suture. According to one example, the pull handle includes two separable portions, each of which has one end of the suture secured thereto.

The self-suturing anchor device has a securement mechanism that is adapted to be actuated by the user to automatically further secure the catheter in a quick and efficient manner. The rotatable ring is used in connection with a ratchet mechanism. The ratchet mechanism allows movement of the rotatable ring in a first direction while controlling movement of the rotatable ring in the opposite direction. As a result, the rotational position of the rotatable ring is secured. The ratchet mechanism includes rotatable ratchet members. The rotatable ratchet members pivot allowing for slight movement of the portion of the rotatable ratchet member having the teeth. Additionally, in one example a ratchet member engagement spring is provided which maintains contact between the teeth of the rotatable ratchet member and the teeth of the ratchet ring. The ratchet member engagement spring can flex or undergo other deformation to allow for sliding of the teeth of the rotatable ratchet member over the teeth of the ratchet ring during rotation of the rotatable ring.

Figure 1:
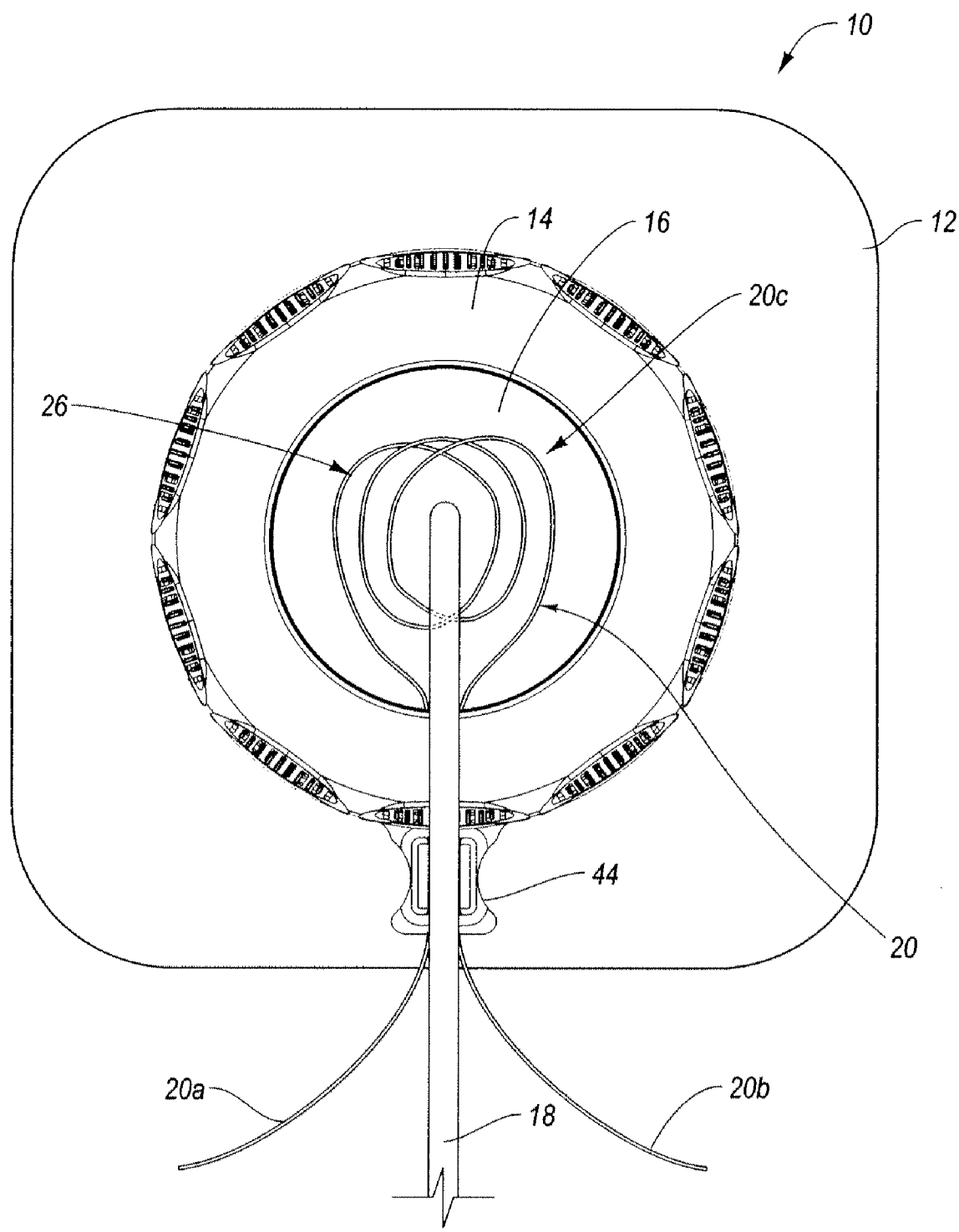
FIG. 1 is a top view of the catheter anchor device illustrating deployment of a first suture.

FIG. 1 is a perspective view of anchor device 10 according to one embodiment of the present invention. Anchor device 10 is utilized to secure a catheter relative to a patient while allowing access to a catheter insertion site for observation and care of the catheter insertion site. Anchor device 10 provides a simple and effective mechanism for securing a catheter by automatically deploying one or more sutures to secure the catheter. In the illustrated embodiment, anchor device 10 comprises an adhesive sheet 12, rotatable ring 14, and a center aperture 16. A catheter 18 is shown being utilized in connection with anchor device 10. Catheter 18 has been inserted into the patient at a catheter insertion site 26.

Anchor device 10 has been placed over catheter 18 such that catheter 18 is threaded through the middle of center aperture 16. Catheter insertion site 26 is positioned approximately in the middle of center aperture 16 such that rotatable ring 14 is positioned and centered about catheter insertion site 26. Adhesive sheet 12 has an adhesive backing that securely fastens anchor device 10 to the patient before and after deployment of the sutures of anchor device 10. Rotatable ring 14 is utilized to automatically deploy one or a plurality of sutures for securement of catheter 18.

Center aperture 16 is configured to allow access to catheter 18 at the catheter insertion site 26. By providing access to catheter insertion site 26, a practitioner can observe the condition of catheter insertion site 26 and provide treatment and care of catheter insertion site 26 as needed. This can be important in the event of injury, infection, drainage, or other disruptions of catheter insertion site 26. The ability to care for catheter insertion site 26 can be quite helpful, particularly where catheter 18 is utilized in a gastric or similar setting where regular care and treatment of the catheter insertion site is necessary to maintain the health of the patient and proper operation of catheter 18.

In the embodiment illustrated in FIG. 1, a first suture 20, which is utilized to secure catheter 18, is shown being partially deployed. First suture 20 comprises a first end 20a, a second end 20b, and a loop portion 20c. A user grasps a pull handle connected to each of the first end 20a and second end 20b. Exemplary pull handles will be discussed in more detail below. The user then retracts first end 20a and second end 20b with the pull handle in a rearward fashion to draw the loop portion 20c of the first suture 20 from under the rotatable ring 14 and to partially deploy the loops of the loop portion 20c of first suture 20. In the illustrated embodiment, the loop portion 20c of first suture 20 is a double loop forming a clove hitch-type securement knot. At this point of the deployment process, a user actuates rotatable ring 14. After actuating the rotatable ring 14, the user then continues to retract first and second ends 20a, b. As the user retracts first end 20a and second end 20b, loop portion 20c continues to tighten about catheter 18 at a position adjacent rotatable ring 14. The configuration of first suture 20 provides a simple, quick, and effective mechanism for securing a portion of catheter 18 relative to rotatable ring 14. In a matter of seconds, first suture 20 can be freed from beneath the rotatable ring 14. A second suture 21 (FIG. 2) may then be deployed by actuating rotatable ring 14. In one example, preliminarily freeing the loop portion 20c of the first suture 20 allows the rotatable ring 14 to be rotated with less torque, thereby facilitating deployment of the second suture 21. After the second suture 21 is fully deployed and securely fastened about catheter 18, first end 20a and second end 20b can retracted to secure the loop portion 20c adjacent the bottom of rotatable ring 14. Next, the ends 20a, b may then be tied about the portion of catheter 18 adjacent the extension saddle 44. By providing two points of securement, first suture 20 minimizes twisting and/or pulling of catheter 18 that could result in injury of the patient tissue at catheter insertion site 26.

As will be appreciated by those skilled in the art, a variety of types and configurations of anchor devices can be utilized without departing from the scope and spirit of the present invention. For example, in one embodiment, only a first suture is utilized to secure the catheter. In another embodiment, string is used in the place of conventional suture material. In yet another embodiment, the suture is comprised of a monofilament material, woven silk thread, or other known or conventional string, wire, and/or suture materials.

Figure 2:
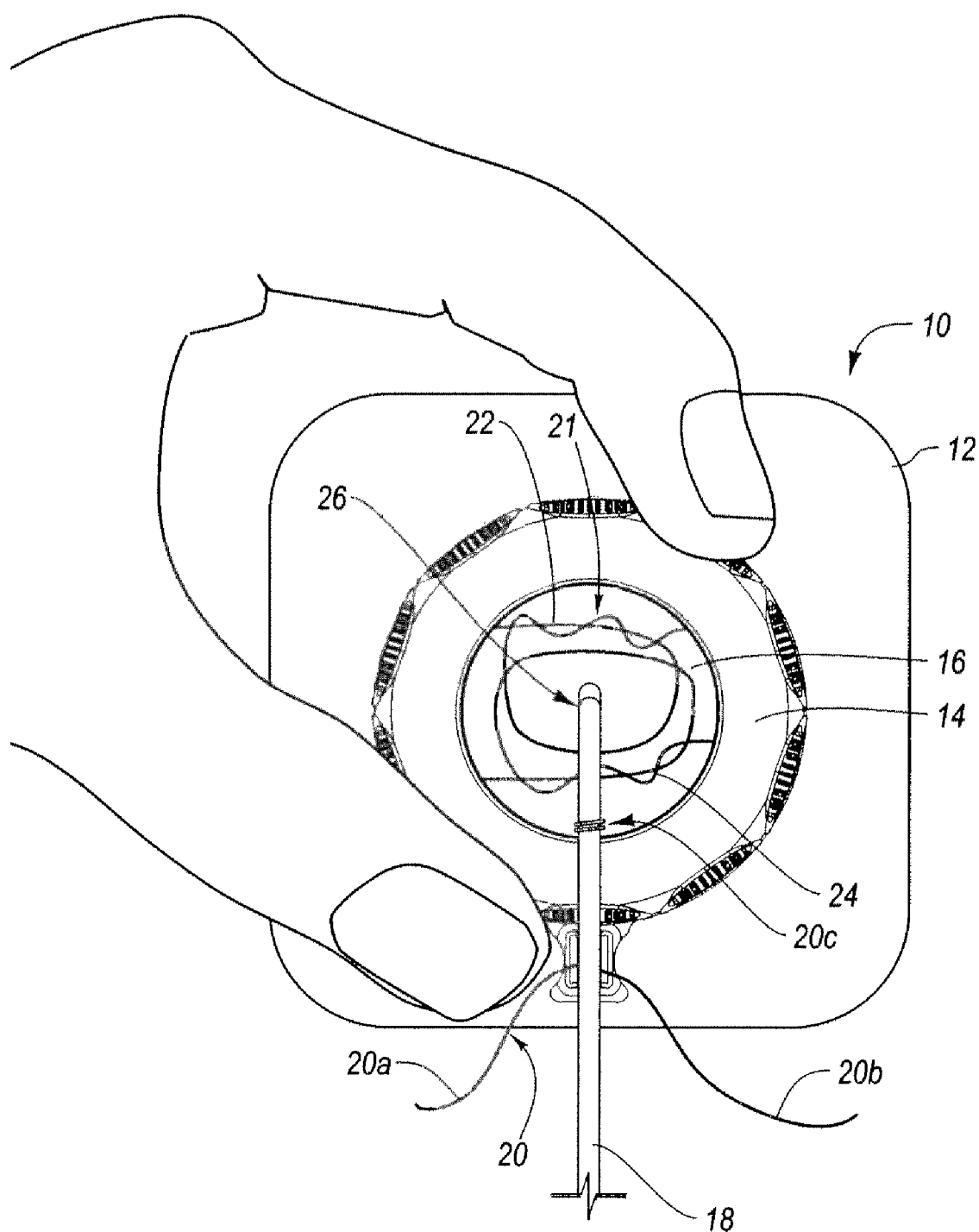
FIG. 2 is a top view of the catheter anchor device illustrating deployment of a second suture relative to the catheter.

FIG. 2 is a top view of anchor device 10 illustrating a user actuating rotatable ring 14 of anchor device 10, according to one embodiment of the present invention. In the illustrated embodiment, anchor device 10 includes a second suture 21 with a first portion 22 and a second portion 24, both of which are housed beneath rotatable ring 14 prior to actuation of rotatable ring 14. Once the loop portion 20c of first suture 20 is freed from beneath the rotatable ring 14, a user begins to rotate rotatable ring 14 to deploy first portion 22 and second portion 24 of second suture 21. As the user rotates rotatable ring 14, first portion 22 and second portion 24 automatically deploy from beneath rotatable ring 14 and begin to loop about the portion of catheter 18 adjacent catheter insertion site 26. In the illustrated embodiment, the ends of first portion 22 and second portion 24 of second suture 21 are actuated from opposite sides of rotatable ring 14 such that both first portion 22 and second portion 24 of second suture 21 anchor catheter 18 from opposite sides of the catheter insertion site 26. As a result, two lateral securement positions are provided on each side of catheter 18 to minimize unintentional movement of catheter 18 at catheter insertion site 26. Securement of catheter 18 at catheter insertion site 26 will be discussed in more detail with respect to FIG. 3. The loops of first portion 22 and second portion 24 of second suture 21 are formed using a double or triple knot configuration to provide a slip resistant knot when secured to catheter 18. The ability of the loop portion to secure catheter 18 will be discussed in more detail with respect to FIG. 3.

As will be appreciated by those skilled in the art, a variety of types and configurations of anchor device 10 can be utilized without departing from the scope and spirit of the present invention. For example, multiple sutures can be provided in connection with deployment of the rotatable ring rather than a single suture. In another embodiment, more than two sutures are provided in connection with deployment of rotatable ring 14. In yet another embodiment, a plurality of rotatable rings are provided with each rotatable ring deploying one or more sutures to secure catheter 18 in subsequent steps of actuation during use of the anchor device.

Figure 3:
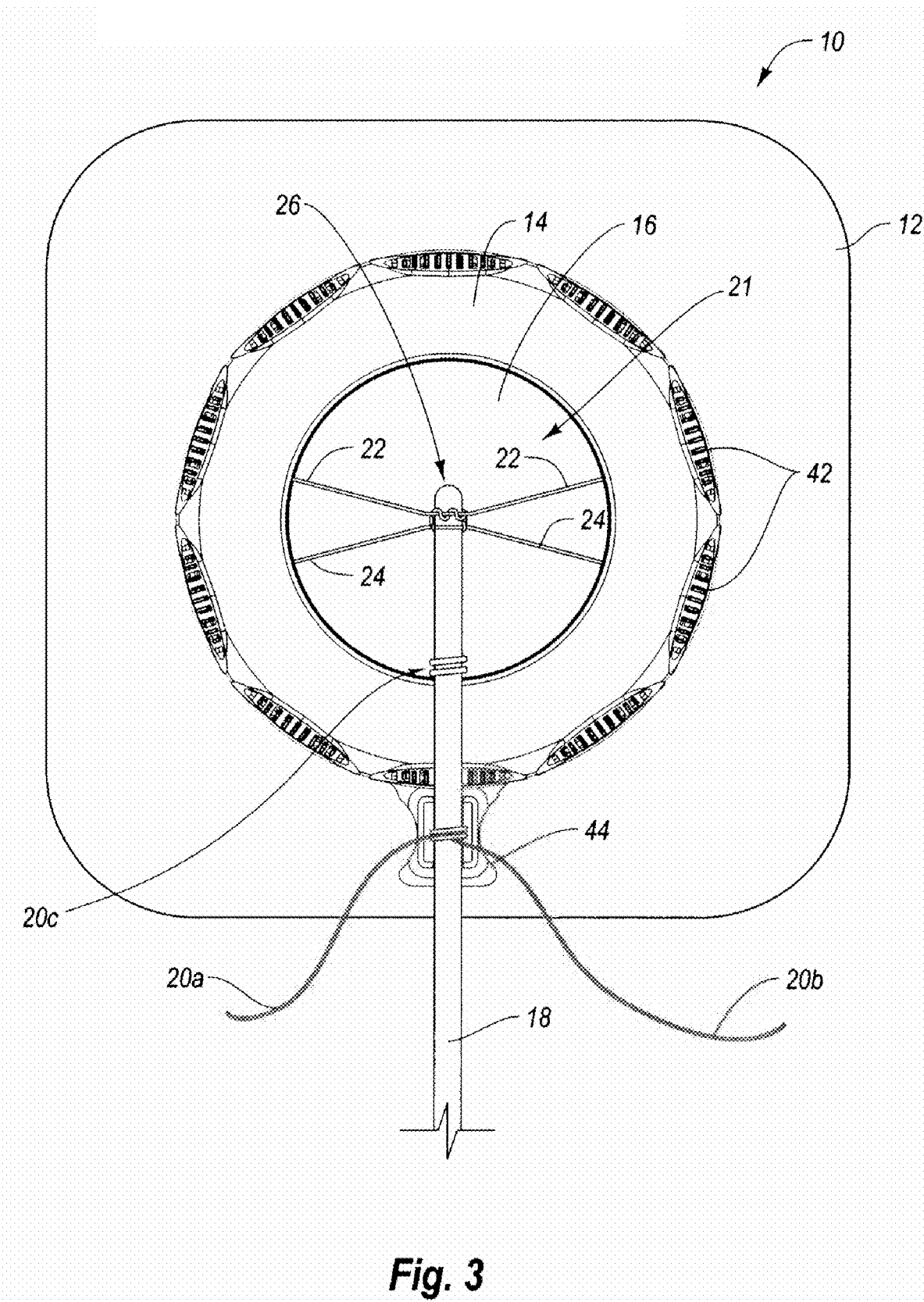
FIG. 3 is a top view of a catheter anchor device illustrating securement of the catheter subsequent to deployment of the sutures.

FIG. 3 is a top perspective view of anchor device 10 subsequent to deployment of rotatable ring 14 and securement of first suture 20. In the illustrated embodiment, catheter 18 is secured by the first and second portions 22, 24 of the second suture 21, subsequent to actuation of rotatable ring 14. Once second suture 21 has been deployed, the first suture 20 may be further secured by retracting the first and second ends 20*a, b* to tighten loop portion 20*c*. The first and second ends 20*a, b* may then be tied adjacent extension saddle 44. Extension saddle 44 provides a desired degree of displacement between the points of securement provided by suture 20 relative to catheter 18. The displacement provided between the points of securement of first suture 20 is sufficient to substantially minimize kinking, twisting, or other manipulation of catheter 18 that could result in damage to the patient tissue at catheter insertion site 26 resulting from movement of catheter 18. Additionally, extension saddle 44 provides a groove that accommodates catheter 18 to minimize kinking, pinching, or other pressure on catheter 18 from the transition over the top of rotatable ring 14.

The portion of catheter 18 positioned adjacent catheter insertion site 26 is secured by second suture 21. Particularly, one part of first portion 22 is positioned on the left side of rotatable ring 14, while another part of first portion 22 is secured adjacent the right side of rotatable ring 14. Similarly, one part of second portion 24 is secured adjacent the left side of rotatable ring 14, while another part of second portion 24 is secured adjacent the right side of rotatable ring 14. Additionally, the first portion 22 and second portion 24 on the left side of rotatable ring 14 are positioned at a displacement between five and 65 degrees or more relative to one another to provide securement of catheter 18 and thereby minimize movement of catheter 18 during use of the anchor device 10. Similarly, the first portion 22 and second portion 24 on the right side of rotatable ring 14 are positioned at an angle of between five and 65 degrees or more relative to one another to minimize movement of catheter 18 which could result in injury at catheter insertion site 26. As a result, a total of four separate points of securement are provided at the portion of catheter 18 adjacent catheter insertion site 26 to minimize both lateral and forward and rearward movement of catheter 18 during usage of catheter anchor device 10. This provides a safe and reliable securement of catheter 18 during usage while also providing access to the catheter insertion site for cleaning and care of the catheter and/or patient tissue at catheter insertion site 26. In the illustrated embodiment, a plurality of scallops 42 are shown on rotatable ring 14. Scallops 42 facilitate gripping of rotatable ring during actuation of rotatable ring as shown in FIG. 2. Scallops 42 comprise a concave depression in the outward surface of rotatable ring 14. By providing a concave depression in the outward surface of rotatable ring 14, scallops 42 provide gripping members that minimize any potential abrasion to the patient or practitioner utilizing anchor device 10.

The configuration of anchor device 10 and rotatable ring 14 allow for quick, simple, and effective securement of catheter 18 subsequent to placement of catheter 18 in a patient. This not only shortens the length of the catheter securement procedure and thus the entire catheter placement procedure, but also is sufficiently simple such that an assisting nurse or other caretaker can secure catheter 18 while the physician attends to other aspects of the procedure being performed. This is not only more efficient from the standpoint of operating room economics, but can also be quite helpful in time-sensitive procedures such as in a trauma setting or emergency situation.

Figure 4:
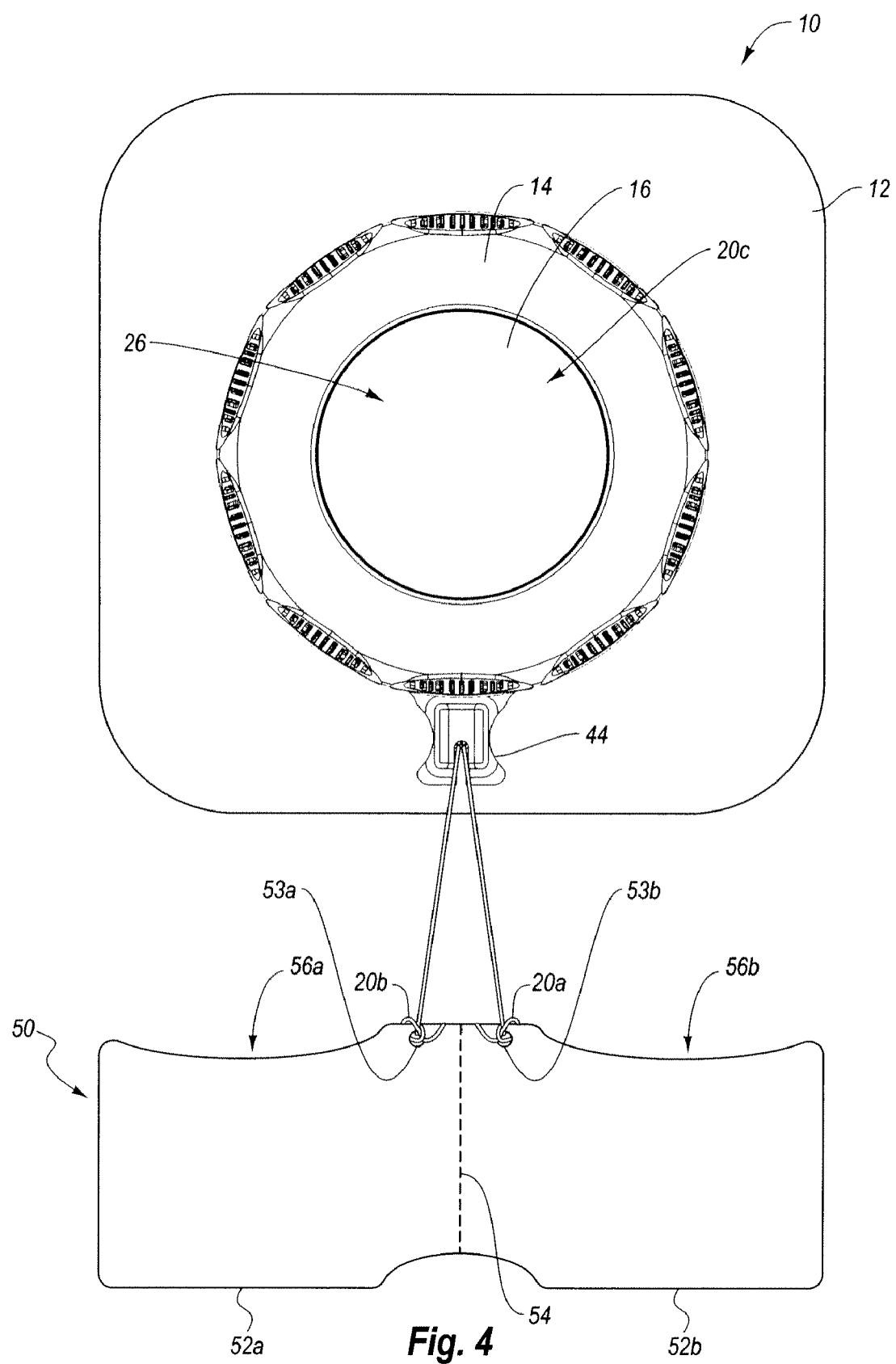
FIG. 4 is a top view of an example anchor device that includes a pull handle.

FIG. 4 is a top view of an example embodiment of an anchor device 10 that includes a pull handle 50. Pull handle 50 facilitates the rapid deployment of first suture 20 to secure loop portion 20*c* to catheter 18 and the rotatable ring 14. As will be evident from the disclosure herein, the various disclosed embodiments of a pull handle are example structural implementations of a means for tensioning a suture. The scope of the invention is not, however, limited to the disclosed structural implementations. Rather, any other structure(s) of comparable functionality are considered to fall within the scope of the invention.

In the illustrated example, pull handle 50 includes first and second separable members, such as pull tabs 52*a, b*. Pull tabs 52*a, b* each have respective openings 53*a, b* defined therein. The ends 20*a, b* of first suture 20 are shown as being looped through the openings 53*a, b* and secured to pull tabs 52*a, b*. As a result, each end 20*a, b* of the first suture 20 is secured to a corresponding separable tab 52*a, b*. Pull tabs 52*a, b* are initially coupled together. In particular, according to the example shown, pull handle 50 is initially a single piece of material with two separable portions. In the illustrated example, pull handle 50 includes a line of perforations 54 disposed between the pull tabs 52*a, b*. However, the scope of the invention is not so limited. More generally, any portion of material that can be separated into at least two parts can be used for the pull handle 50.

Figure 5:
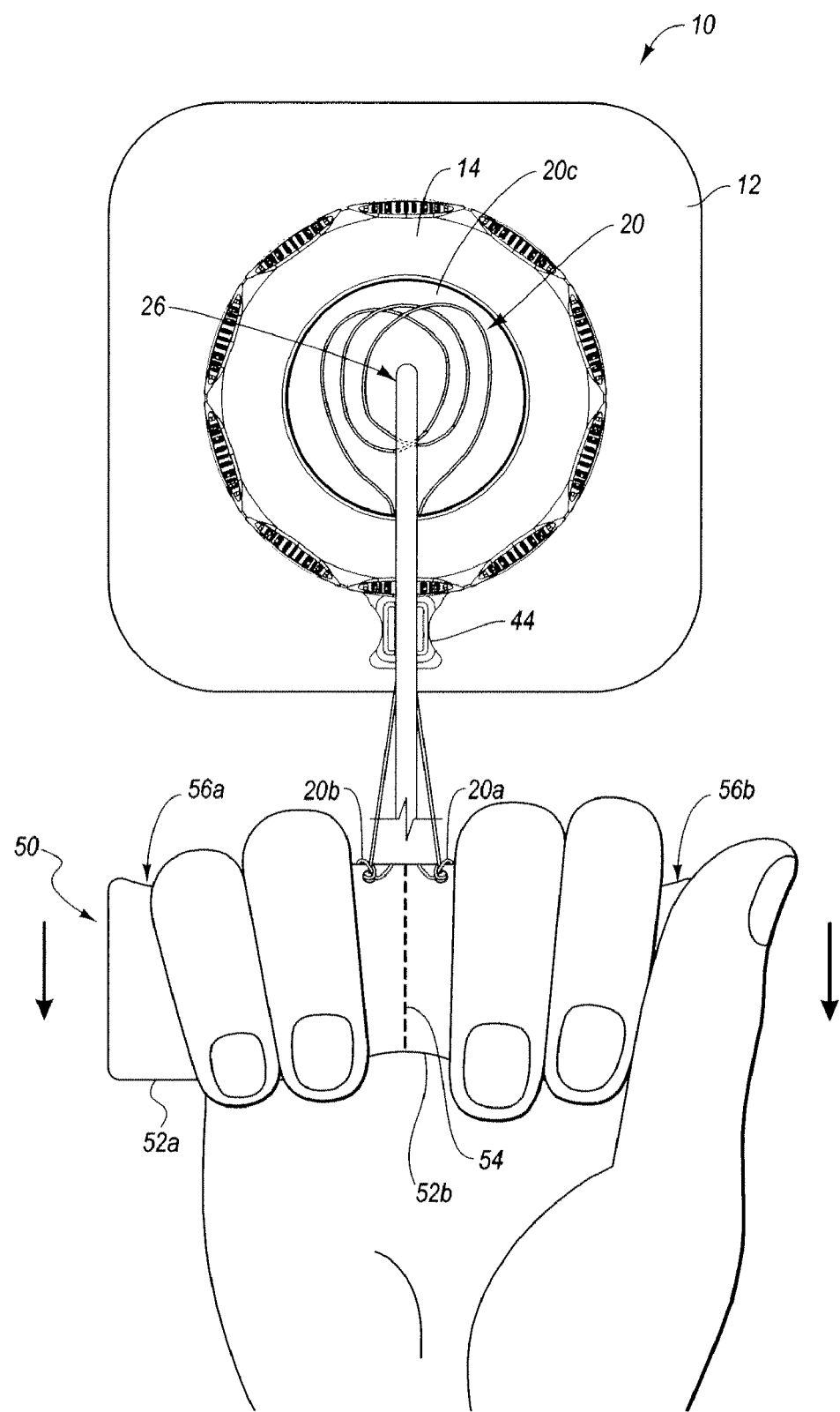
FIG. 5 illustrates the deployment of the loop portion of the first suture.

FIG. 5 illustrates the deployment of the loop portion 20*c* of first suture 20. In order to operate the illustrated example device, a practitioner deploys the loop portion 20*c* by first grasping the pull tabs 52*a, b* as shown. At this point, the loop portion 20*c* is surrounding catheter 18, in a similar manner as illustrated in FIG. 1. The practitioner then draws the pull handle 50 away from the rotatable ring 14. Drawing pull handle 50 away from rotatable ring 14 draws the loop portion 20*c* from underneath the rotatable ring 14. Additionally, after second suture (FIG. 3) is deployed, the pull handle 50 may also be retracted to draw the first and second ends 20*a, b* of the first suture 20 more tightly about catheter 18 at a position adjacent rotatable ring 14.

To aid in the operation of pull handle 50, one or both of pull tabs 52*a, b* may include ergonomic features. For example, each of the example pull tabs 52*a, b* includes a gripping edge 56*a, b* that has a generally arcuate profile. A generally arcuate profile may be more comfortable for a practitioner to grasp when deploying the loop portion 20*c*. Further, the generally arcuate profiles shown mean that the pull tabs 52*a, b* are wider on the outer portions of the pull tabs 52*a, b* than in the center. The generally wider outer portions may reduce the possibility that a practitioner's grip will slip while pulling on pull handle 50. Further, the pull tabs 52*a, b* may be shaped such that pull handle 50 is substantially symmetrical. Symmetry of pull handle 50 may allow for use of the pull handle 50 with either hand.

Figure 6:
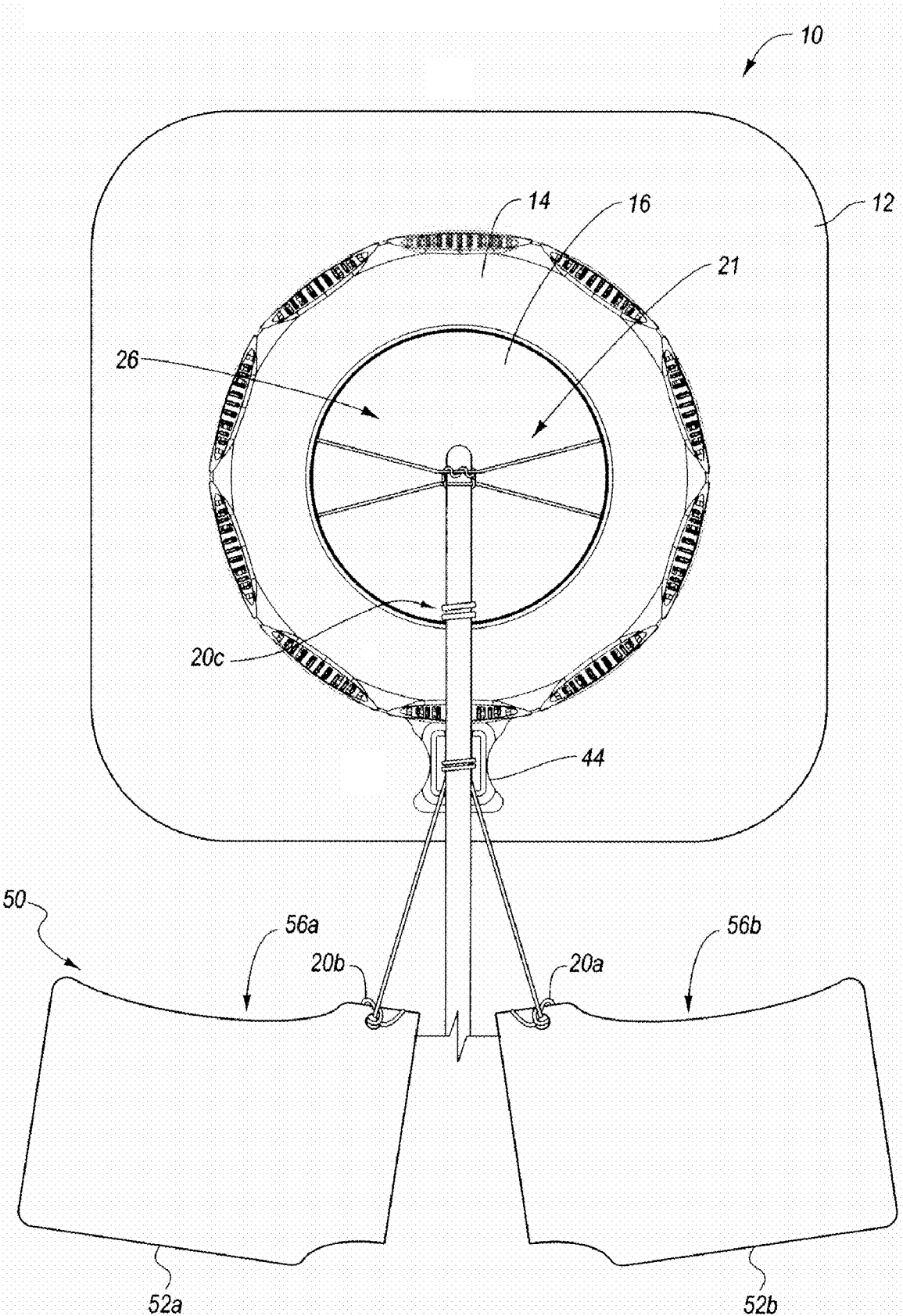
FIG. 6 illustrates the first and second ends of the first suture tied to the portion of catheter corresponding with extension saddle.

Turning now to FIG. 6, when loop portion 20*c* is freed from beneath the rotatable ring 14, the rotatable ring 14 may be actuated to deploy second suture 21. Once second suture 21 is fully deployed, first end 20*a* and second end 20*b* can then be tied about the portion of catheter 18 located proximate the extension saddle 44. In particular, as previously introduced, pull handle 50 includes separable pull tabs 52*a, b* or other portions that may otherwise be separated into at least two pieces. Once the loop portion 20*c* is freed and second suture 21 is deployed, the pull handle 50 may be retracted to tighten loop portion 20*c* about the catheter 18 at a location proximate the rotatable ring 14. The pull tabs 52*a, b* are then separated.

Next, each pull tab 52a, b may be manipulated independently to tie the second knot in the first suture 20 to fully secure the first suture 20, such as a knot near the portion of the catheter 18 located proximate with the extension saddle 44. In the illustrated embodiment, the pull handle 50 may be formed of a material capable of being manually torn along the perforation line 54a, b. Suitable materials may include, without limitation, pulp products such as high-density paper or fiber board.

Figure 7:
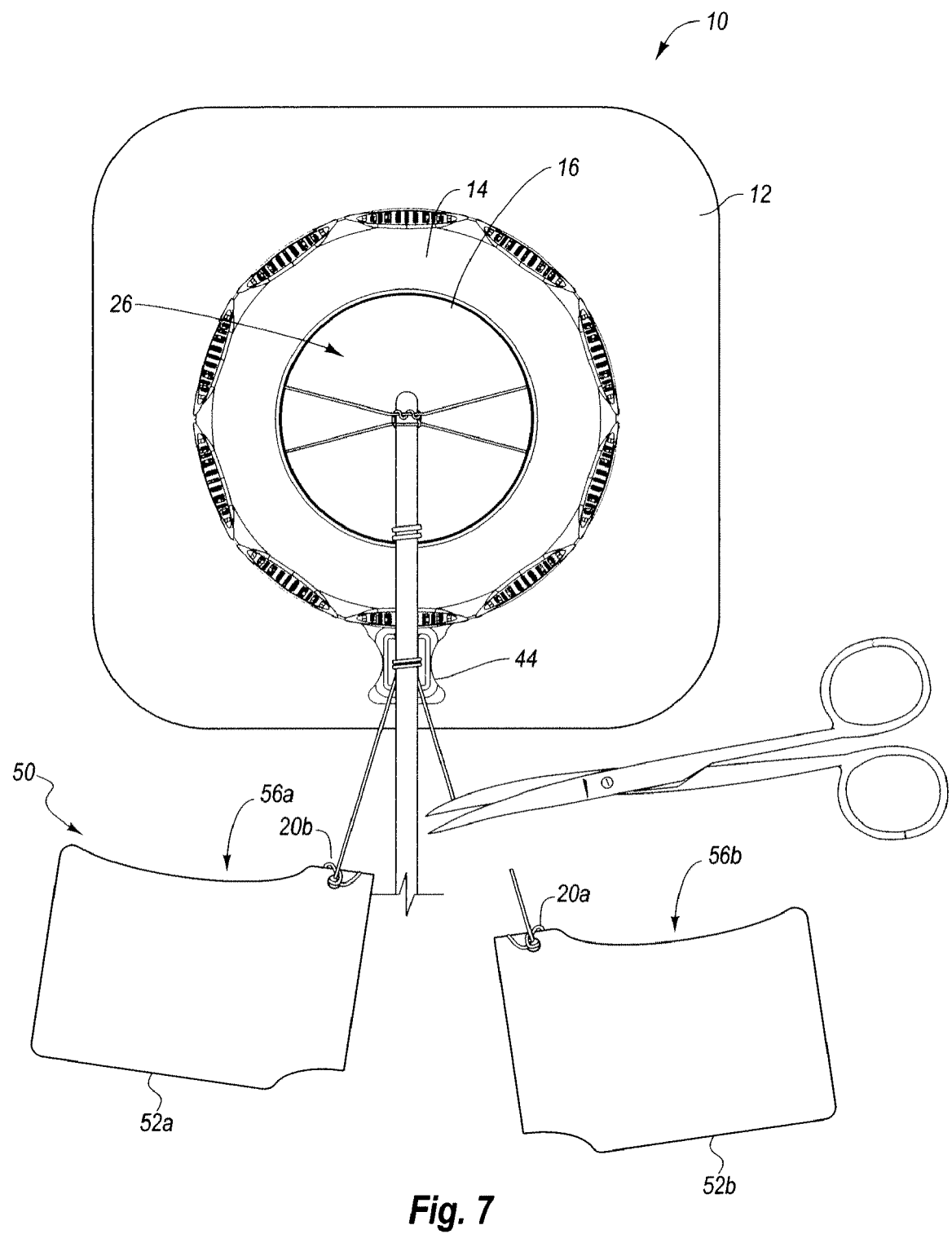
FIG. 7 illustrates the pull tabs being removed from the first suture.

FIG. 7 illustrates the pull tabs 52a, b being removed from the first suture 20. As introduced, the pull tabs 52a, b may be separated to facilitate tying of the second knot. It may be desirable to remove the pull tabs 52a, b and/or reduce the length of the first and second ends 20a, b that extend beyond the extension saddle 44. The pull tabs 52a, b may provide a convenient handle relative to bare suture ends thereby allowing a practitioner to quickly shorten the lengths of the first and second ends 20a, b while removing the pull tabs 52a, b. According to the illustrated example, scissors or another cutting tool may be used to cut the first and second ends 20a, b. While one configuration of pull handle 50 has been disclosed, those of skill in the art will appreciate any number of configurations are possible. Another example configuration is disclosed in FIGS. 8A to 8B.

Figure 8A:
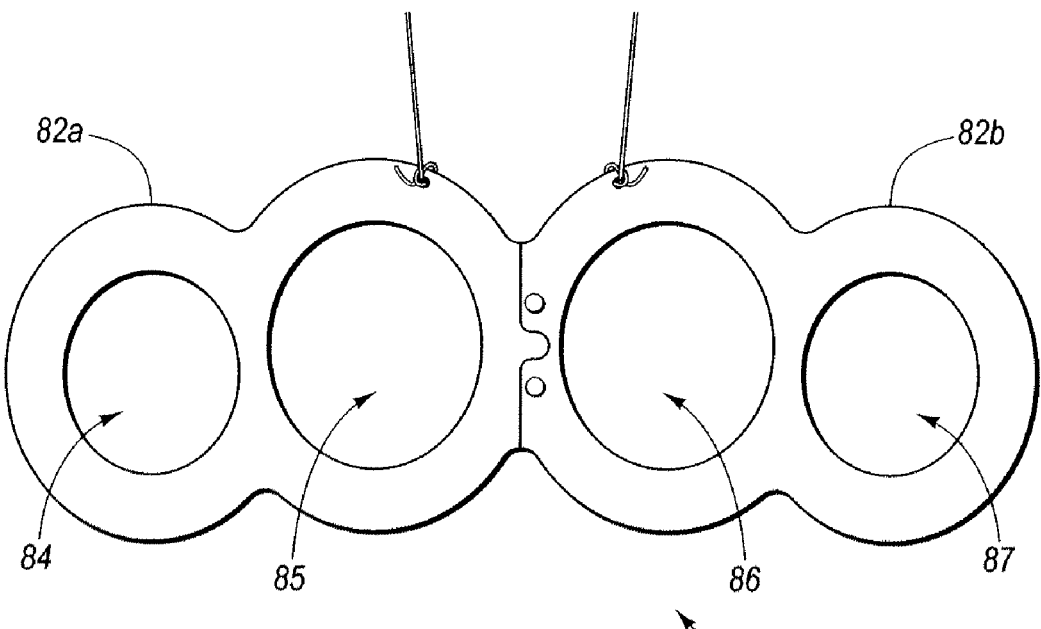
FIG. 8A illustrates a pull handle that includes first and second pull tabs.

FIG. 8A illustrates a pull handle 80 that includes first and second pull tabs 82a, 82b. For ease of reference, the first pull tab 82a will be discussed as being located on the left hand side. Each pull tab 82a, b includes apertures 84-87 formed therein. The apertures 84-87 are sized to allow a practitioner to grasp the pull handle 80 by passing her fingers therethrough. The pull handle 80 then may be actuated as discussed above to secure a loop portion 20c (FIG. 1) of a first suture 20 to a catheter. Once the loop portion 20c is thus secured, the pull tabs 82a, b may be separated.

Figure 8B:
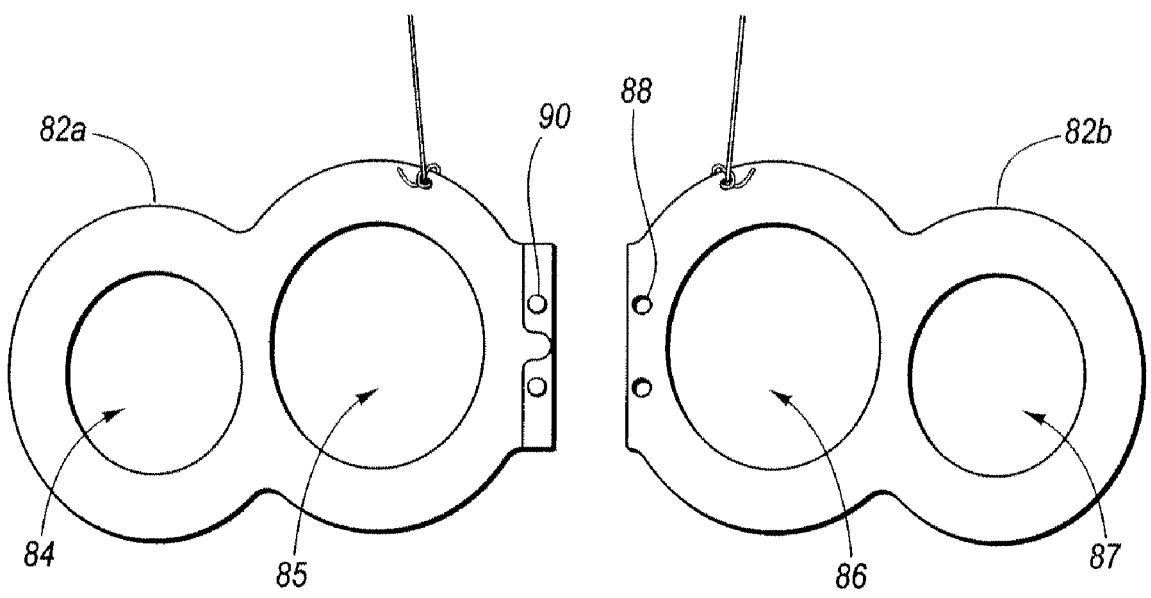
FIG. 8B illustrates the pull tabs separated.

FIG. 8B illustrates the pull tabs 82a, b separated. According to the illustrated embodiment, the pull tabs 82a, b have interlocking structure(s) formed thereon that are configured to mate with corresponding structure(s) on the other pull tab. This configuration allows for re-use of the handle 80. Such a configuration may provide a relatively secure coupling of the pull tabs 82a, b while also providing for convenient and rapid separation of the pull tabs 82a, b and/or release of the sutures 20, 21. According to one example, the pull tabs 82a, b may be formed of a durable material, such as a plastic material. Further, the pull tabs 82a, b may be formed using any suitable process or processes, such as molding processes.

According to one example, the interlocking structures formed on the pull tabs 82a, b include recesses 88 and posts 90. The posts 90 are pressed into the recesses 88 to thereby couple the pull tabs 82a, b together. While posts and recesses are described, any interlocking arrangement may also be used.

Figure 8C:
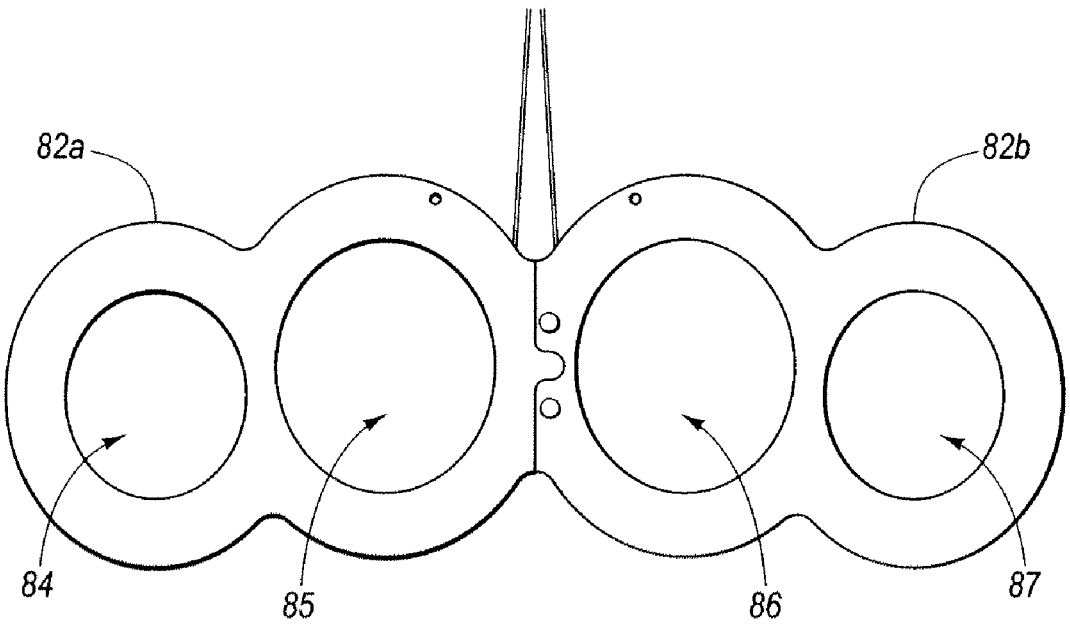
FIG. 8C illustrates sutures secured to a pull handle with first and second pull tabs.
Figure 8D:
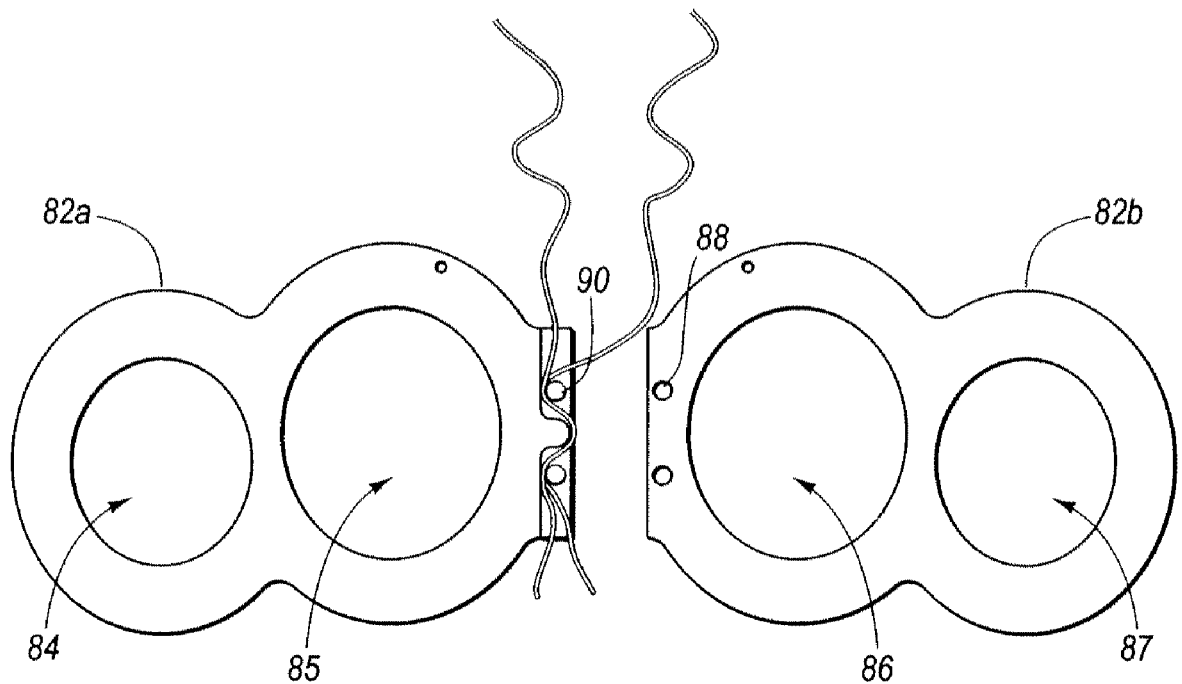
FIG. 8D illustrates the first and second pull tabs separated and the sutures freed.

FIGS. 8C and 8D illustrate another example in which first and second ends 20a, b of the suture 20 are secured between the pull tabs 82a, b. In particular, as previously discussed, the pull tabs 82a, b are coupled together using an interlocking structures. The first and second ends 20a, b may be located between the interlocking structures, such as before the pull tabs 82a, b are coupled together. In particular, in one example the first and second ends 20a, b of the sutures are placed adjacent the posts 88 before the posts 90 are coupled to the recesses 88. Locating the first and second ends 20a, b between pull tabs 82a, b secures the first and second ends 20a, b to the pull tabs 82a, b.

FIG. 8D illustrates the pull tabs 82a, b separated from each other. Separating the first and second pull tabs 82a, b frees the first and second ends 20a, b of the first suture 20. After the first and second ends 20a, b are freed, they may be tied directly, thereby eliminating the need to further free the first and second ends 20a, b from the pull tabs, such as by cutting.

Figure 9:
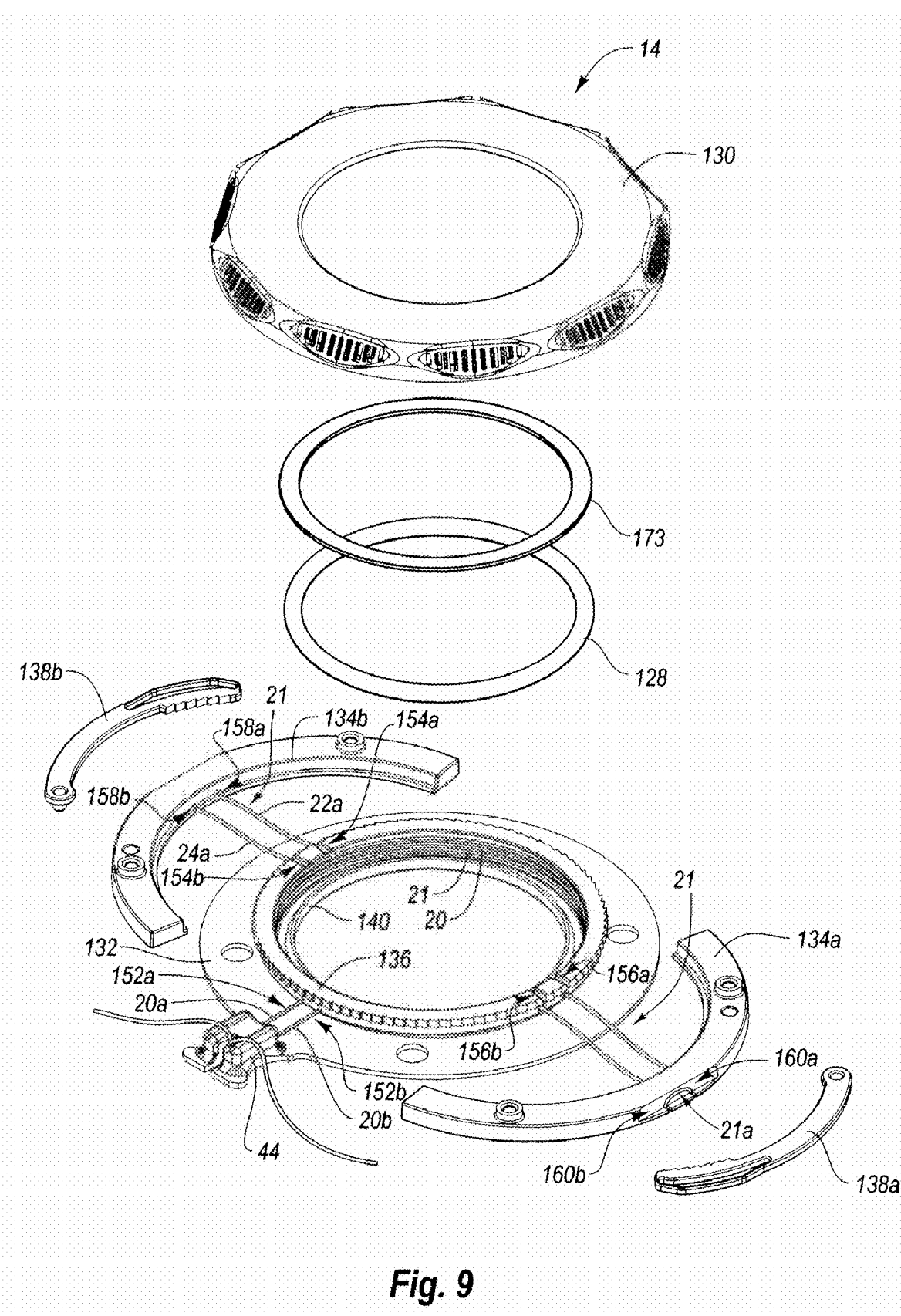
FIG. 9 is an exploded view of the catheter anchor device illustrating the components of the catheter anchor device including an O-ring and rotatable ratchet members.

FIG. 9 is an exploded view of rotatable ring 14 of anchor device 10 depicting a ratchet mechanism. In the illustrated embodiment, rotatable outer ring 130 and bearing members 134a, b are shown separated from base 132. A plurality of pin members are positioned beneath rotatable outer rings. The pin members are configured to be positioned in bearing members 134a, b to secure bearing members 134a, b to rotatable outer ring 130.

Bearing members 134a, b are configured to be positioned between rotatable outer ring 130 and base 132. Bearing members 134a, b contact base 132 beneath ratchet ring 136 such that bearing members 134a, b do not contact the teeth of ratchet ring 136. Similarly, bearing members 134a, b contact rotatable outer ring 130 beneath rotatable ratchet members 138a, b such that bearing members 134a, b do not contact the teeth of rotatable ratchet members 138a, b. As a result, bearing members 134a, b do not interfere with the cooperative engagement between ratchet members 38a, b and ratchet ring 136.

A lip on each of bearing members 134a, b extends inwardly beneath ratchet ring 136. When rotatable outer ring 130 is secured to bearing members 134a, b, the lateral positioning of bearing members 134a, b secures both bearing members 134a, b and rotatable outer ring 130 to base 132. Additionally, the positioning of bearing members 134a, b maintains ratchet members 138a, b in cooperative engagement with ratchet ring 136. In the illustrated embodiment, bearing members 134a, b include a securement member for securing the first and second portions 22, 24 of the second suture 21 during rotation of bearing members 134a, b.

As will be appreciated by those skilled in the art, a variety of types and configurations of bearing members can be utilized without departing from the scope and spirit of the present invention. For example, in one embodiment a circular bearing member is utilized in place of two bearing member segments. In another embodiment, one or more bearing members are integrally coupled to the rotatable outer ring. In yet another embodiment one or more bearing members are integrally coupled to the ratchet members. In another embodiment, the bearing members are positioned above the ratchet ring. In yet another embodiment, a liquid bearing mechanism is utilized. In another embodiment, a roller bearing mechanism is utilized.

In the embodiment illustrated in FIG. 9, the path of sutures 20, 21 relative to sutures storage channel 140 previous to deployment is depicted. Sutures 20, 21 are looped such that they are positioned inside suture storage channel 140. As a result, when the practitioner secures the anchor device to the patient, the practitioner does not need to manage the positioning of sutures 20, 21. Suture storage channel 140 in combination with O-ring 128 also maintains the particular desired loop formation of sutures 20, 21 ensuring proper operation and/or deployment of sutures 20, 21.

In the embodiment illustrated in FIG. 9, first suture channels 152a, b are positioned through base 132 and exit at extension saddle 44. First suture 20 is configured to be positioned through first suture channels 152a, b such that the ends of first suture 20a, b extend from extension saddle 44. The extension of the ends of first suture 20a, b from the extension saddle 44 allows a user to grasp the ends of first suture 20a, b to actuate first suture 20.

Second suture channels 154a, b and third suture channels 156a, b are positioned through ratchet ring 136 and base 132. Bearing member suture channels 158a, b and 160a, b are positioned through bearing members 134a, b. More particularly, the second suture 21 is looped to form the first and second portions 22, 24 that intersect at loop portion 21a. The loop portion 21a of the second suture 21 is secured to the exterior of bearing member 134a. Next, the first and second portions 22, 24 of the second suture 21 are passed through bearing member 134a, then through the ratchet ring 136 and base 132. Loops are then formed in the first and second portions 22, 24 of second suture 21 as described below with reference to FIGS. 12A and 12B. After the loops are formed in the first and second portions 22, 24, the first and second portions 22, 24 are passed through bearing member 134b. In particular, a first end 22a of first portion 22 is threaded first through bearing member channel 160a in bearing member 134a and through third suture channel 156a. The first portion 22 of second suture 21 is then looped as desired. The first end 22a of the first portion 22 is then passed through the second suture channel 154a in ratchet ring 136 and base 132 and through bearing member channel 158a. Similarly, a first end 24a of the second portion 24 is threaded first through bearing member channel 160b in bearing member 134a and then through third suture channel 156b. The second portion 24 of second suture 21 is then looped as desired. The first end 24a of the second portion 24 is then threaded through second suture channel 154b in ratchet ring 136 and base 132 and finally through bearing member channel 158b. The first ends 22a, 24a of the first and second portions 22, 24 of the second suture are then secured to the exterior of bearing member 134b.

With continuing reference to FIG. 9, base 132 and ratchet ring 134 are stationary relative to the rotatable outer ring 130. As a result, second suture channel 154a, b and third suture channel 156a, b remain stationary during operation of rotatable ring 14. Bearing members 134a, b rotate in connection with rotatable outer ring 130. As a result, bearing member suture channels 158a, b and 160a, b rotate in connection with rotation of rotatable outer ring 130 and bearing member 134a, b. When bearing members 134a, b rotate in a clockwise direction, the ends 22a and 24a of the second suture 21 are drawn around the outside diameter of base 132 beneath ratchet ring 136. As a result, the length of first and second portions 22 and 24 of the second suture 21 inside suture storage channel 140 is shortened. As the length of first and second portions 22 and 24 inside suture storage channel 140 is shortened, the loops of sutures 22 and 24 become smaller such that they can no longer fit in suture storage channel 140. This results in automatic deployment of the second suture 21 from suture storage channel 140.

Rotatable ratchet members 138a, b engage the teeth of ratchet ring 136 to minimize counterclockwise movement of rotatable ring 14 that would result in loosening of the second suture. During rotation of rotatable outer ring 130, bearing members 134a, b and rotatable ratchet members 138a, b are rotated in a clockwise direction about base 132 and in particular ratchet ring 136. Rotatable ratchet members 138a, b engage the teeth of ratchet ring 136 as rotatable ratchet members are advanced 138a, b in the clockwise direction. When a user discontinues rotation of rotatable outer ring, rotatable ratchet members 138a, b engage the teeth of ratchet ring 136 minimizing movement of rotatable outer ring in a counter-clockwise direction that would otherwise loosen first portion 22 and second portion 24.

As illustrated in FIG. 9, rotatable ratchet member 138a is positioned between bearing member 134a and rotatable outer ring 130. A pivot pin is positioned on the bottom surface of each of the rotatable ratchet members 138a, b. The pivot pins are positioned in rotation bores of the corresponding bearing members 134a, b to pivotally couple rotatable ratchet member 134a to bearing member 134a. Rotatable outer ring 130 contacts the upper surface of rotatable ratchet member 138a to maintain contact between the pivot pins and the rotation bores.

The end of rotatable ratchet members 138a, b positioned opposite the pivot point provided by the pivot pin of rotatable ratchet member 138a, b and the bore of bearing members 134a, b include a spring member and a plurality of teeth. The plurality of teeth engage the teeth of ratchet ring 136 to minimize movement of rotatable outer ring 130 and bearing members 134a, b in a counterclockwise direction. This spring is provided by the cutaway portion in the head of rotatable ratchet members 138a, b and the resilient nature from the material from which the heads of rotatable ratchet members 138a, b are constructed. Rotatable ratchet members 138a, b will be discussed in more detail with reference to FIGS. 13A and 13B.

In the embodiment illustrated in FIG. 9, an O-ring 128 is also illustrated. O-ring 128 is configured to be sandwiched between rotatable outer ring 130 and base 132 to maintain the position of first suture 20, first portion 22 and second portion 24 of the second suture 21 beneath rotatable ring 14. By maintaining the position of first suture 20, first portion 22, and second portion 24, disruption of the sutures before deployment of the sutures is minimized and reliable and proper operating of anchor device 10 is maintained. As a result, O-ring 128 provides a simple and reliable mechanism for storing first suture 20, first portion 22, and second portion 24 beneath rotatable ring 14 during storage of anchor device 10, during securement of adhesive sheet 12 to the patient, or other aspects of the securement procedure performed before actuation of sutures 20, 21. A backup ring 173 is also provided between the O-ring 128 and rotatable outer ring 130. The backup ring 173 isolates the rotation of the rotatable outer ring 130 and the O-ring 128 to reduce torque and friction.

Figure 10A:
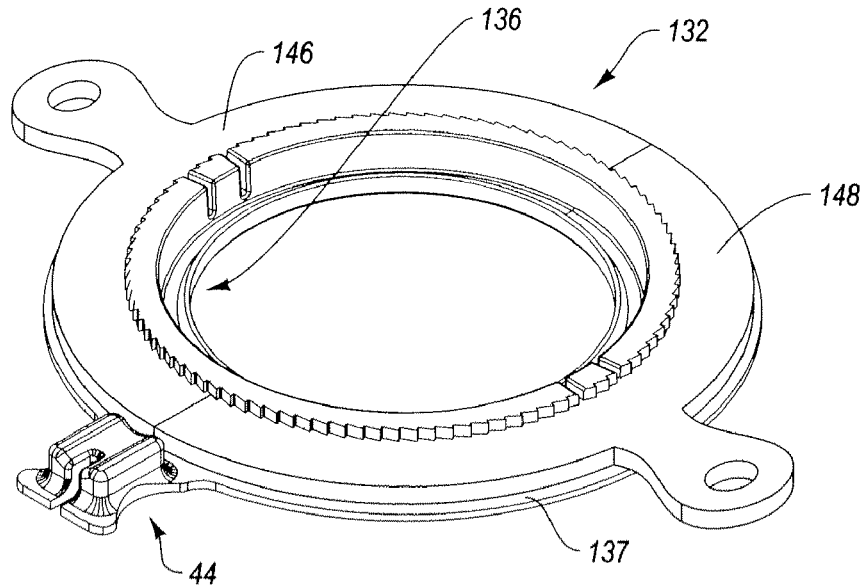
FIGS. 10A and 10B are perspective views of the base of the catheter anchor device illustrating molding of the base utilizing first and second mold members.
Figure 10B:
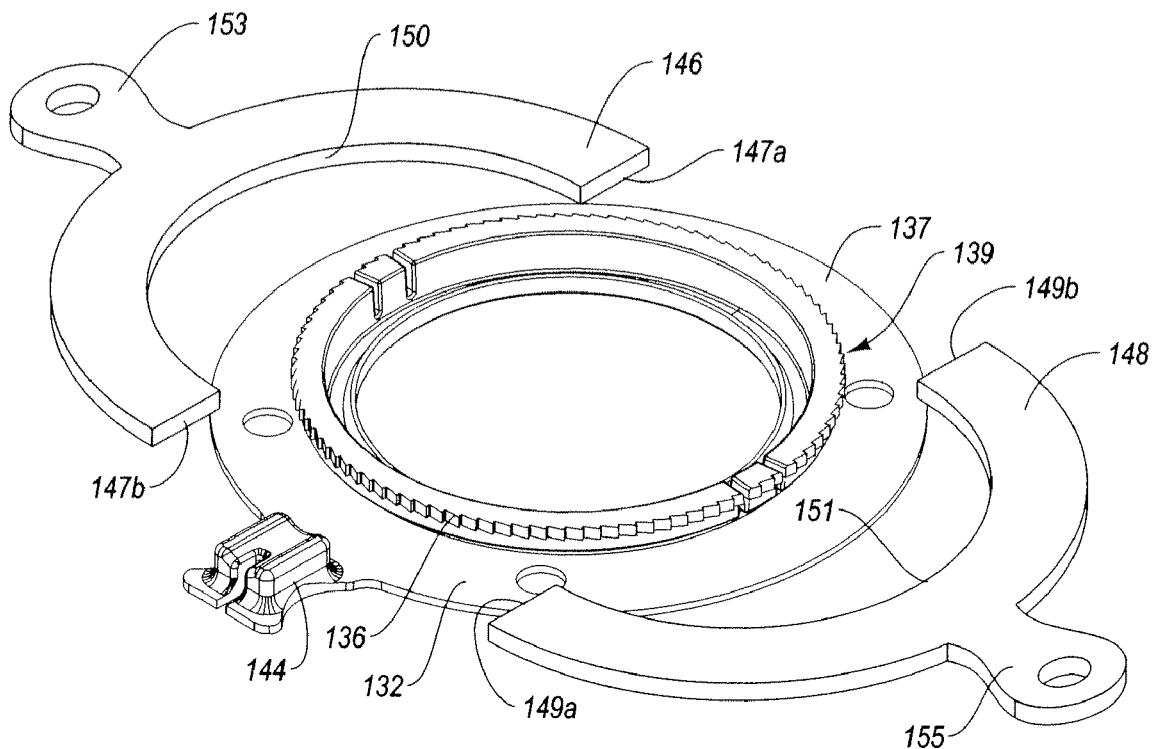

FIGS. 10A and 10B are perspective views of base 132 during molding of base 132. In the illustrated embodiment, base 132 comprises a single molded member formed utilizing first and second mold members 146 and 148. Base 132 comprises a ratchet ring 136 and an extension saddle 44. In the illustrated embodiment, base 132 includes an undercut 139 positioned between ratchet ring 136 and base flange 137. Undercut 139 substantially complicates the molding of base 132. As a result, first mold member 146 and second mold member 148 are utilized to provide the undercut during the molding of base 132. For the sake of clarity, the other mold members utilized to form base 132 have not been illustrated to more clearly depict operation of first mold member 146 and second mold member 148.

In the illustrated embodiment, first mold member 146 comprises mold member interfaces 147a, b, an inner circumference 150, and a gripping handle 153. Second mold member 148 comprises mold member interfaces 149a, b, an inner circumference 151, and gripping handle 155. During molding, mold member interfaces 147a, b of first mold member contact mold member interfaces 149a, b of second mold member 148. Inner circumference 150 of first mold member 146 and inner circumference 151 of second mold member 148 form the undercut 139 positioned between ratchet ring 136 and base flange 137. Inner circumference 150 and inner circumference 151 define the inner boundary of undercut 139. The top portion of first mold member 146 and second mold member 148 define the upper lateral surface extending from the innermost horizontal surface of uppercut 139 (not shown) to the edge of ratchet ring 136. The bottom of first mold member 146 and second mold member 148 form the lower horizontal surface which extends from the inner vertical surface of undercut 139 (not shown) and extends outward to be coextensive with base flange 137.

In one embodiment, the surfaces of undercut 139 are slightly flared or tapered to allow for proper releasing of first mold member 146 and second mold member 148 such that when a user grasps gripping handles 153 and gripping handle 155 to pull first mold member 146 and second mold member 148 in a rearward direction, first mold member and second mold member 146, 148, automatically release and can easily be slid from undercut 39. In this manner, base 132 can be molded in single member ensuring continuity of surfaces and reliable and proper operation of the components of base 132 during use of anchor device 10.

As will be appreciated by those skilled in the art, a variety of types and configurations of mechanism can be utilized to mold base 132 in a unitary fashion without departing from the scope and spirit of the present invention. For example, first and second mold members which are configured to be automatically retracted by an automated molding apparatus or other machinery can be utilized. In another embodiment, a single mold member which is hinged, bendable, meltable or otherwise manipulable to remove the mold member from undercut 139 is utilized. In another embodiment, mold members having different form, size, and/or surfaces can be utilized. In another embodiment, more than two mold members are utilized to form the undercut and/or other portions of the base during molding.

Figure 11:
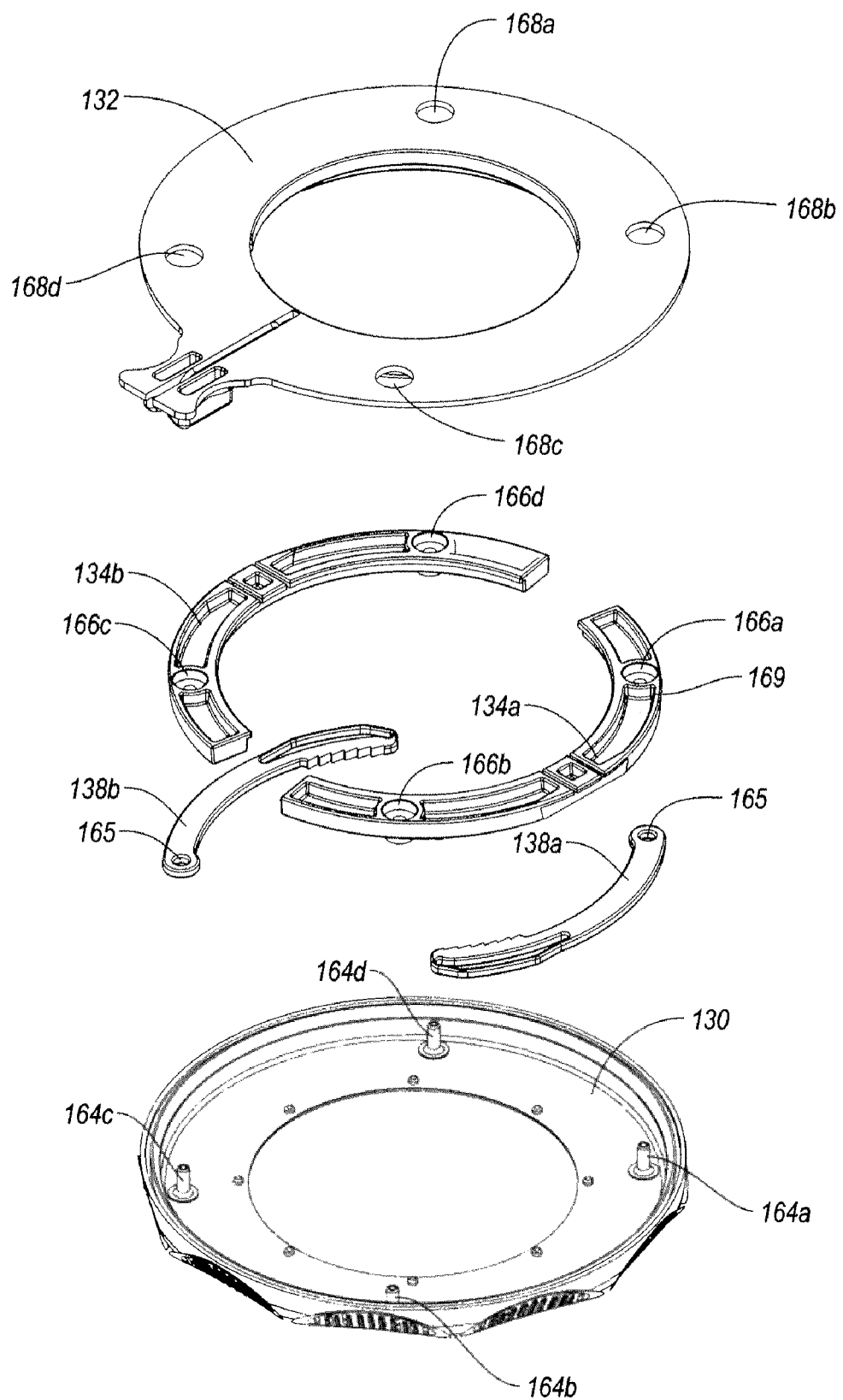
FIG. 11 is an exploded view of the catheter anchor device illustrating components of the catheter anchor device that facilitate assembly of the catheter anchor device utilizing welding of one or more portions of the catheter anchor device.

FIG. 11 is a bottom exploded view illustrating the manner in which the components of anchor device 10 are secured during assembly. In the illustrated embodiment, rotatable outer ring 130, rotatable ratchet member 138a, bearing member 134a, and base 132 are depicted. Bearing member 134a is configured to be sandwiched between rotatable outer ring 130 and base 132. Rotatable ratchet member 138a is configured to be positioned between bearing member 134a and rotatable outer ring 130. Bearing member 134a is configured to be attached directly to rotatable outer ring 130 while being slidable relative to base 132. Pins 164a-c are positioned on the underside of rotatable outer ring 130 engage securement bores 166a-d of bearing member 134a, b. Contact between bearing member 134a and base 132 maintains contact between securement bores 166a-d and pins 164a-d. In the illustrated embodiment, pins 164a, b are configured to be welded to securement bores 166a, b to couple bearing member 134a to rotatable outer ring 130 subsequent to assembly of rotatable outer ring and base 132. Pins 164c, d are configured to be welded to securement bores 166c, d to integrally couple bearing member 134b to rotatable outer ring 130 subsequent to assembly of rotatable outer ring and base 132. A plurality of access bores 168a-d are provided in connection with base 132 such that the welding tool can be inserted through access bores 168a-d to weld pins 164a-d to securement bores 166a-d of bearing members 134a, b.

Rotatable ratchet member 138a is positioned between bearing member 134a and rotatable outer ring 130. In the illustrated embodiment, a pivot pin is positioned on the upper surface of bearing member 134a. The pivot pin is positioned in rotation bore 165 to pivotally couple rotatable ratchet member 134a to bearing member 134a. Rotatable outer ring 130 contacts the upper surface of rotatable ratchet member 138a to maintain contact between the pivot pins and rotation bore 165. Additionally, the outer horizontal portion of the rotatable outer ring which extends downward adjacent rotatable ratchet member 138a contains lateral movement of the free end of rotatable ratchet member 138a to ensure proper operation and contact between the teeth of rotatable ratchet member 138a and the teeth of ratchet ring 136 (illustrated in FIGS. 10A and 10B).

As will be appreciated by those skilled in the art, a variety of types and configurations of mechanisms for securing the components of the rotatable ring can be utilized without departing from the scope and spirit of the present invention. For example, in one embodiment, the bearing member is configured to be welded to the rotatable outer ring previous to assembly with the base. In another embodiment, a snap fitting is provided between the bearing member and the rotatable outer ring. In another embodiment, a continuous bearing member is integrated with the base 132 while the rotatable ratchet member is secured independently to the rotatable outer ring. In yet another embodiment, a surface is provided on the bearing member to maintain proper operation of the rotatable ratchet member.

Figure 12A:
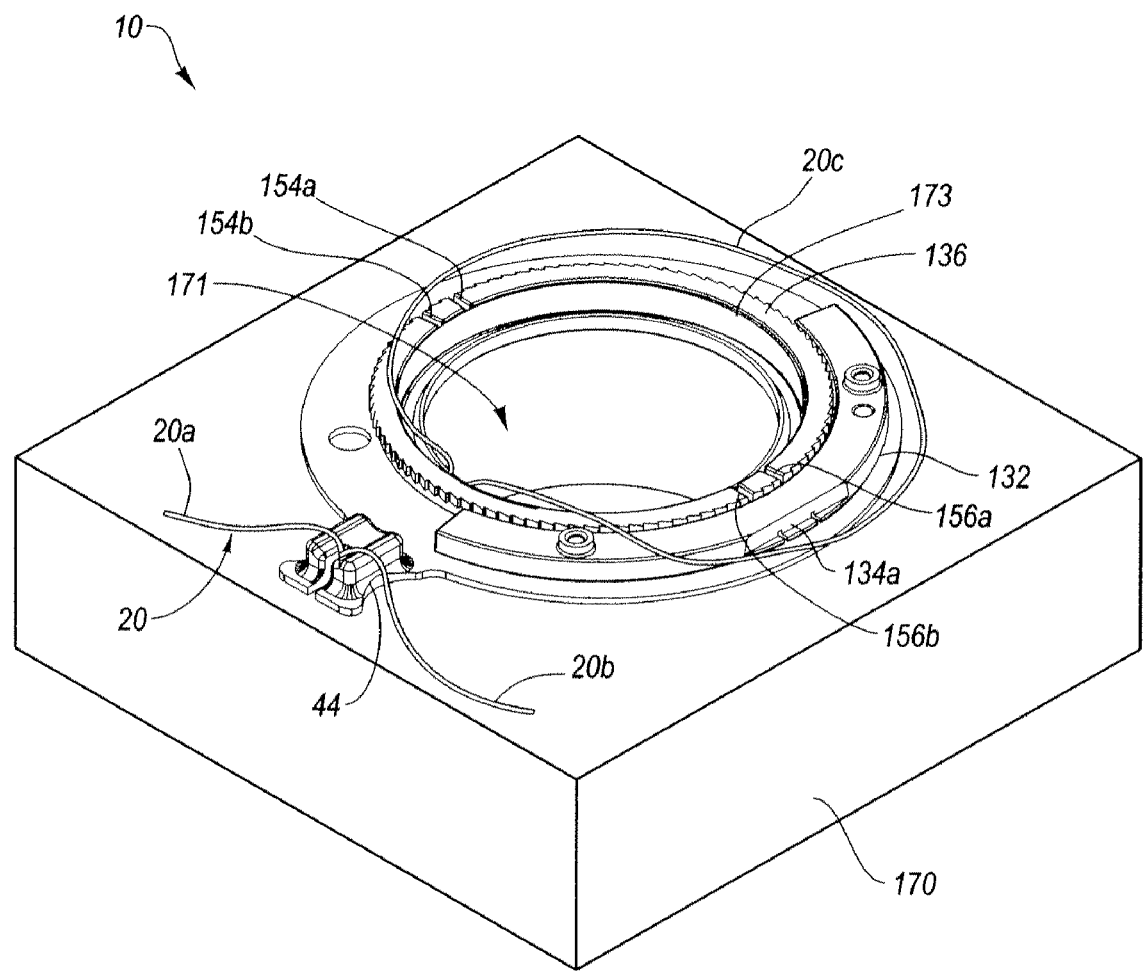
FIGS. 12A and 12B are perspective views of the base of the catheter anchor device illustrating loading of the sutures during assembly of the catheter anchor device.
Figure 12B:
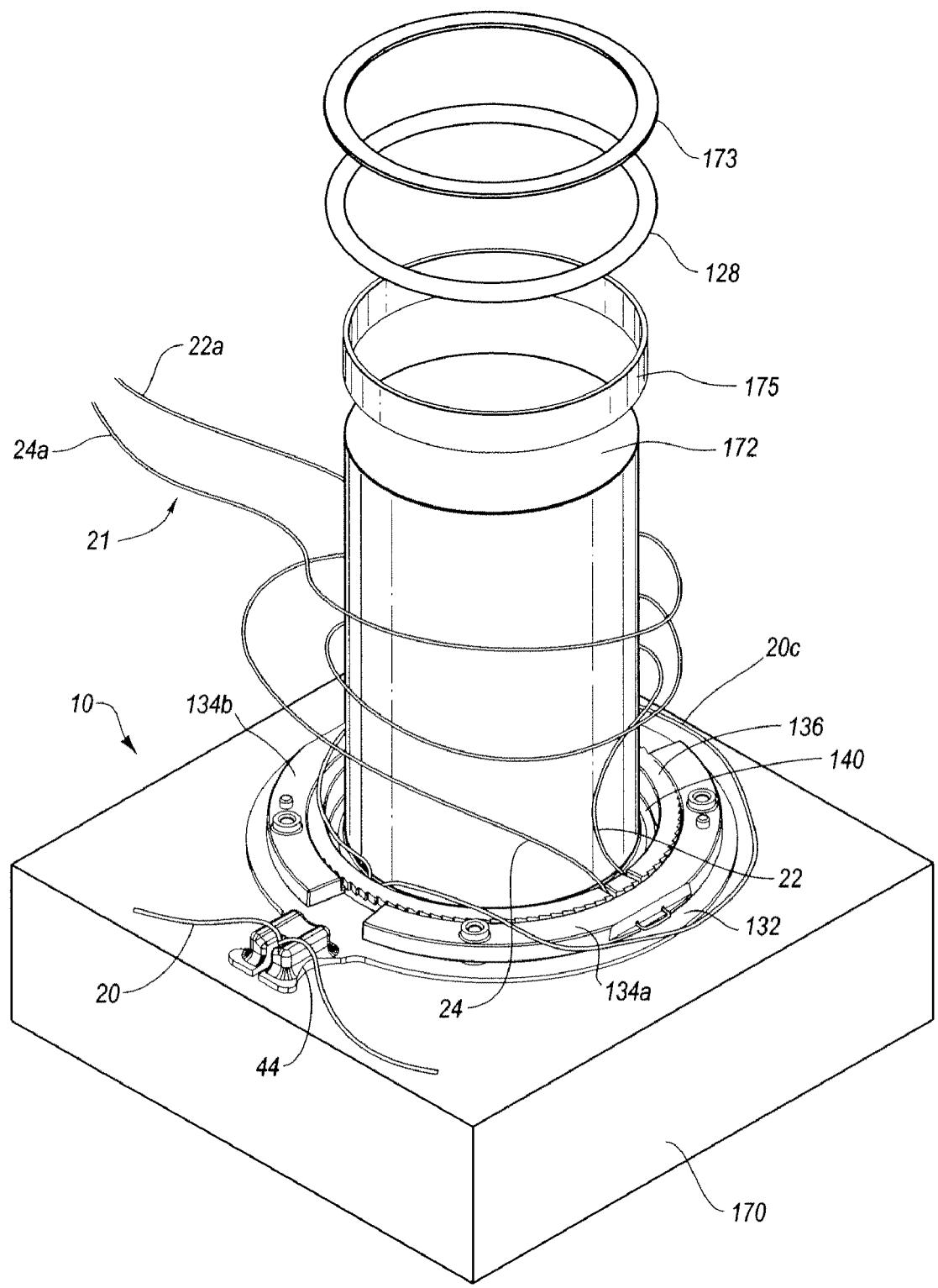

FIGS. 12A and 12B illustrate loading of the sutures utilized with anchor device 10, according to one embodiment of the present invention. In particular, as seen in FIG. 12A, base 132 of anchor device 10 is mounted on a loading block 170. The anchor device 10 is positioned over the center bore 171 of loading block 170. First suture 20 is partially loaded into the base 132. More specifically, the ends 20a, b of first suture 20 are threaded from the interior of the ratchet ring 136 through the base 132 to extend beyond the extension saddle 44. The loop portion 20c of first suture 20 is looped about the perimeter of the base 132. The first and second ends 20a, b may be threaded through the extension saddle 44 either before or after the base 132 is mounted to a loading block 170. Thereafter, the second suture 21 may be loaded.

As illustrated in FIG. 12B, a suture loading cylinder 172 is positioned through center bore 171 (FIG. 12A) such that the wall of the suture loading cylinder 172 is positioned adjacent the inner portion of ratchet ring 136. Suture loading cylinder 172 is utilized to provide a quick and effective mechanism for forming the loop configurations of first suture 20 and second suture 21 and for loading the sutures 20, 21 in base 132. A sleeve 175, also referred to as a suture expander, may also be placed over the suture loading cylinder 172 adjacent the suture loading channel 140. The sleeve 175 may help ensure the loops of the first and second sutures 20, 21 are located within the suture storage channel 140 during loading.

In the illustrated embodiment, the loops of second suture 21 are being formed around suture loading cylinder 172. First suture 20 has previously been threaded through base 132. Initially, the second suture 21 is doubled over to form the first and second portions 22, 24 (FIG. 12A) that are connected by a loop portion. More particularly, as illustrated in FIG. 9, the first end 22a of first portion 22 is threaded first through bearing member channel 160a in bearing member 134a and through third suture channel 156a in the ratchet ring 136 and base 132. A first end 24a of the second portion 24 is threaded first through bearing member channel 160b in bearing member 134a and through third suture channel 156b in the ratchet ring 136 and base 132. Returning to FIG. 12B, after the first ends 22a, 24a, of the first and second portions 22, 24 of the second suture 21 have been threaded through the ratchet ring 136 and base 132, loops are formed in the first and second portions 22, 24. One loop is substantially formed by wrapping the length of first portion 22 about suture loading cylinder 172 in a manner so as to produce the desired loop configuration in the first portion 22 of the second suture 21. The second portion 24 is also wrapped to form the desired loop configuration. Once the loops have been formed in the first and second portion 22, 24, the ends 22a, 24a of the second suture 21 are threaded through the ratchet ring 136 and base 132 and then the bearing member 134b and secured.

As the loops of first and second portions 22, 24 are drawn tight and the loop portion 21 a is secured relative to bearing members 134a and base 132, the loops of the first and second portions 22, 24 of the second suture 21 are automatically drawn down such that the loops are loaded within ratchet ring 136 in the desired position for deployment. Once second suture 21 has been loaded into the base 132, additional loops or knots may be formed in the first suture 20 using the suture loading cylinder 172. The first suture 20 may then be drawn tight such that the first suture 20 is drawn into the suture storage channel 140. As will be appreciated by those skilled in the art, similar steps, acts, and processes are utilized to load first suture 20 and second portion 24. The discussion of the formation of loops in the second suture and the loading of second suture 21 in base 132 is discussed for illustrative purposes and should in no way be considered to be limiting in nature.

Once first and second sutures 20 and 21 have been properly loaded in base 132, O-ring 128 is positioned over the top of suture loading cylinder 172. O-ring 128 is lowered along the length of suture loading cylinder 172 until the O-ring 128 is positioned along the inner circumference of ratchet ring 136, effectively maintaining the position of first suture 20, first portion 22, and second portion 24 in their desired position within base 132. Once O-ring 128 has been properly positioned within base 132, a backup ring 173 is lowered along the length of suture loading cylinder 172 until the backup ring 173 is positioned on top of the O-ring 128.

After the O-ring 128 and backup ring 173 have been positioned, the suture loading cylinder 172 is withdrawn and rotatable outer ring 130 is lowered into engagement with base 132 as discussed with respect to FIG. 11. The proper steps can then be taken to couple rotatable outer ring 130 to bearing member 134a, b as discussed with respect to FIG. 11. The backup ring 173 isolates the rotation of the rotatable outer ring 130 and the O-ring 128 to reduce torque and friction. The backup ring 173 may be formed of a material having a relatively low coefficient of friction, such as a durable plastic or polytetrafluoroethylene (PTFE). Further, when positioned as described above, the O-ring 128 and the backup ring 173 are located between the rotatable outer ring 130 and the base 132. In the illustrated example, the backup ring 173 is located between the O-ring 128 and the rotatable outer ring 130. In this position, as the rotatable outer ring 130 rotates, the rotatable outer ring 130 is in contact with the backup ring 173. Thus rotation of the rotatable outer ring 130 is not hindered by the O-ring 128. Further, the relatively low friction of the backup ring 173 reduces friction between the O-ring 128 and the backup ring 173. While the backup ring 173 is described as being positioned before the suture loading cylinder 172 is withdrawn, the backup ring 173 may alternatively be positioned over the O-ring 128 after the suture loading cylinder 172 is withdrawn.

As will further be appreciated by those skilled in the art, a variety of types and configurations of mechanism for loading the sutures in the base can be utilized without departing from the scope and the spirit of the present invention. For example, in one embodiment, a loading block and suture loading cylinder are utilized to manually load the sutures in the anchor device. In another embodiment, the loading block and suture loading cylinder are utilized with automated processes to load the suture into the base or other component of the anchor device.

Figure 13A:
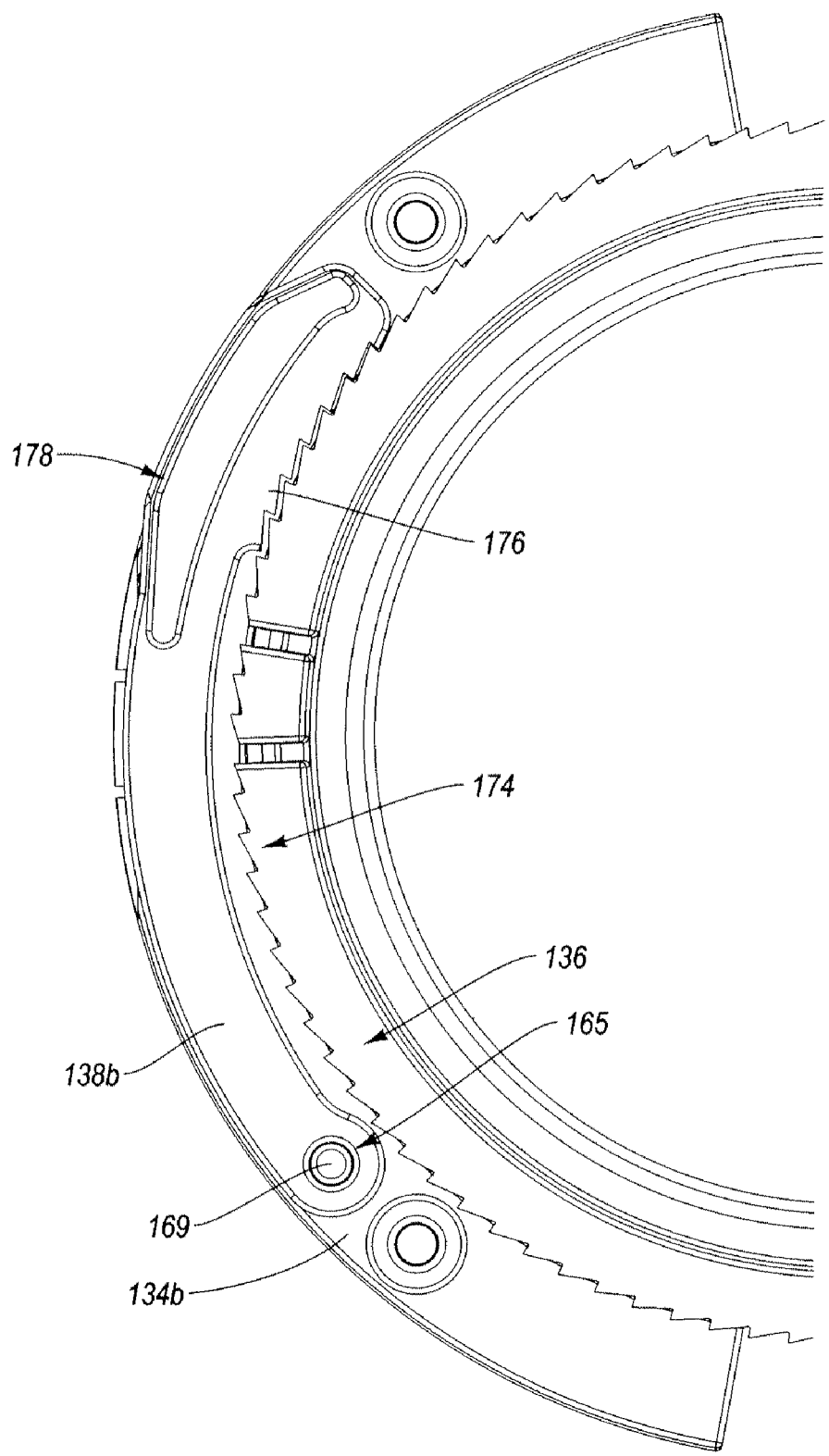
FIGS. 13A and 13B are component views illustrating the ratchet mechanism including operation of a rotatable ratchet member relative to the ratchet ring.
Figure 13B:
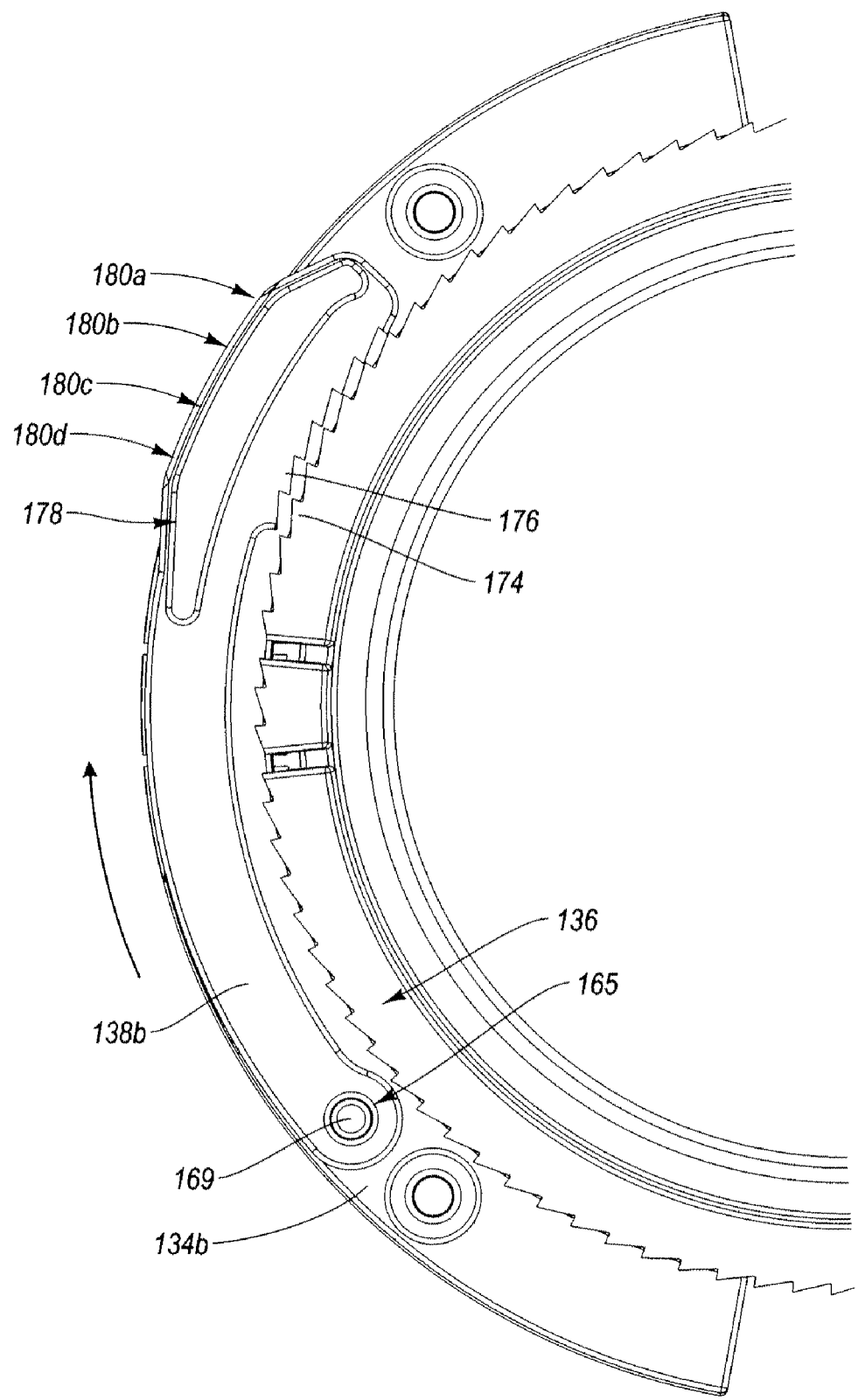

FIGS. 13A and 13B illustrate rotatable ratchet member 138b in operation with respect to ratchet ring 136. While rotatable ratchet member 138b is shown for illustrative purposes, it will be understood by those skilled in the art that operation of rotatable ratchet member 138b also is exemplary of rotatable ratchet member 138a (see FIG. 9). In the illustrated embodiment, rotatable ratchet member 138b is rotatably coupled to bearing member 134b utilizing pivot pin 169 and rotation bore 165 of rotatable ratchet member 134b. Rotatable ratchet member 38a, b engages the teeth of ratchet ring 136 to minimize counterclockwise movement of rotatable ring 14 that would result in loosening of second suture 21. Rotatable ratchet member 138b is secured to bearing member 134b by pivot pin 169 located between the upper surface of bearing member 134b and the bottom surface of rotatable outer ring 130 (see FIG. 9). Pivot pin 169 is positioned in the rotation bore 165 of rotatable ratchet member 138b such that rotatable ratchet member 138b can pivot about pivot pin 169.

The rotatable ratchet member 138b is held in place relative to bearing member 134b by being sandwiched between bearing member 134b and rotatable outer ring 130 (see FIG. 4). Thus, during rotation of rotatable outer ring 130 (see FIG. 4), bearing member 134b and rotatable ratchet member 138b are rotated in a clockwise direction about ratchet ring 136. Rotatable ratchet member 138b engages the teeth of ratchet ring 136 as rotatable ratchet member is advanced 138b in the clockwise direction. When a user discontinues rotation of the rotatable outer ring, rotatable ratchet member 138b engages the teeth of ratchet ring 136 minimizing movement of rotatable outer ring 130 in a counterclockwise direction that would otherwise loosen the sutures.

The end of rotatable ratchet member 138b positioned opposite the rotation bore 165 and pivot pin includes a ratchet member engagement spring 178 and rotatable ratchet member teeth 176. Rotatable ratchet member teeth 176 engage the ratchet ring teeth 174 to minimize movement of the rotatable outer ring and bearing member 134b in counterclockwise direction. Ratchet member engagement spring 178 is provided by the cutaway portion in the head of rotatable ratchet member 138b. The nature of the material from which the head of rotatable ratchet member 138b is constructed provides sufficient resilience to undergo deformation while maintaining contact between rotatable ratchet member teeth 176 and ratchet ring teeth 174.

As the rotatable ratchet member teeth 176 slide over ratchet ring teeth 174, ratchet member engagement spring 178 flexes slightly to maintain contact between rotatable ratchet member teeth 176 and ratchet ring teeth 174. This is caused by the ramp-like configuration of rotatable ratchet member teeth 176 and ratchet ring teeth 174. When the rotatable ratchet member teeth 176 pass over the outer most ridge of ratchet ring teeth 174 such that they engage new teeth, ratchet member engagement spring 178 forces the rotatable ratchet member teeth 176 toward the center of the anchor device 10, thus maintaining engagement with ratchet ring teeth 174.

As will be appreciated by those skilled in the art, a variety of types and configurations of rotatable ratchet members can be utilized without departing from the scope and spirit of the present invention. For example, in one embodiment, the rotatable ratchet members prevent rotation of a rotatable ring in a clockwise direction. In another embodiment, the rotatable ratchet members prevent backward movement of a nonrotational actuation member. In another embodiment, a secondary spring separate from the body of the rotatable ratchet member provides the spring movement of all or part of the rotatable ratchet member.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A catheter anchor device, the catheter anchor device comprising:
   an adhesive element configured to be secured to a patient's skin proximate a catheter insertion site;
   a stationary base secured to the adhesive element;
   a rotatable ring coupled to the stationary base such that the rotatable ring can be rotated by a user relative to the stationary base;
   a first suture coupled to the rotatable ring, the first suture including a loop portion and first and second ends, the loop portion extending about a catheter when the anchor device is in place relative to the catheter insertion site; and
   a pull handle including first and second separable portions, and the pull handle being coupled to the first and second ends of the first suture, the pull handle being configured to selectively tension the first suture,
   wherein as the first suture is tensioned, the first suture engages a portion of the catheter.

2. The catheter anchor device of claim 1, wherein the first and second ends of the first suture are coupled to the first and second separable portions respectively.

3. The catheter anchor device of claim 1, wherein the pull handle comprises a plastic material.

4. The catheter anchor device of claim 1, further comprising additional sutures coupled to the rotatable ring such that a predetermined rotation of the rotatable ring corresponds with a tensioning of the one or more sutures about the catheter.

5. The anchor device of claim 1, wherein the pull handle is substantially symmetrical about a predetermined axis.

6. A catheter anchor device, comprising:
   an adhesive element configured to be secured to a patient's skin proximate a catheter insertion site;
   a stationary base secured to the adhesive element;
   a rotatable ring coupled to the stationary base such that the rotatable ring can be rotated by a user relative to the stationary base;
   a first suture coupled to the rotatable ring, the first suture including a loop portion and first and second ends, the loop portion extending about a catheter when the anchor device is in place relative to the catheter insertion site; and
   a pull handle including first and second separable portions, and the pull handle being coupled to the first and second ends of the first suture, the pull handle being configured to selectively tension the first suture;
   wherein the first and second ends of the first suture are coupled to the first and second separable portions respectively; and
   wherein the pull handle includes perforations defining a boundary between the first and second separable portions.

7. A catheter anchor device, comprising:
   an adhesive element configured to be secured to a patient's skin proximate a catheter insertion site;
   a stationary base secured to the adhesive element;
   a rotatable ring coupled to the stationary base such that the rotatable ring can be rotated by a user relative to the stationary base;
   a first suture coupled to the rotatable ring, the first suture including a loop portion and first and second ends, the loop portion extending about a catheter when the anchor device is in place relative to the catheter insertion site; and
   a pull handle including first and second separable portions, and the pull handle being coupled to the first and second ends of the first suture, the pull handle being configured to selectively tension the first suture;
   wherein each separable portion includes a generally arcuate gripping portion.

8. A catheter anchor device, comprising:
   an adhesive element configured to be secured to a patient's skin proximate a catheter insertion site;
   a stationary base secured to the adhesive element;
   a rotatable ring coupled to the stationary base such that the rotatable ring can be rotated by a user relative to the stationary base;
   a first suture coupled to the rotatable ring, the first suture including a loop portion and first and second ends, the loop portion extending about a catheter when the anchor device is in place relative to the catheter insertion site; and
   a pull handle including first and second separable portions, and the pull handle being coupled to the first and second ends of the first suture, the pull handle being configured to selectively tension the first suture;
   wherein the first and second pull separable portions include respective interlocking features such that coupling the first and second separable portions can be detached from each other.

9. The catheter anchor device of claim 8, wherein the first and second separable portions can be selectively reattached to each other.

10. The catheter anchor device of claim 9, wherein a portion of each of the sutures is stored in a suture storage channel previous to tensioning of the sutures.

11. The catheter anchor device of claim 9, wherein the suture storage channel is positioned in the stationary base.

12. The catheter anchor device of claim 9, wherein the suture storage channel is positioned in the rotatable ring.

13. The catheter anchor device of claim 9, wherein the suture storage channel comprises a flexible flange.

14. The catheter anchor device of claim 12, further comprising an O-ring, wherein the 0-ring secures the sutures in the suture storage channel in cooperation with the flexible flange.

15. The catheter anchor device of claim 14, further comprising a backup ring, the backup ring being interposed between the rotatable ring and the O-ring.

16. A catheter anchor device, comprising:
   an adhesive element configured to be secured to a patient's skin proximate a catheter insertion site;
   a stationary base secured to the adhesive element;
   a rotatable ring coupled to the stationary base such that the rotatable ring can be rotated by a user relative to the stationary base;
   a first suture coupled to the rotatable ring, the first suture including a loop portion and first and second ends, the loop portion extending about a catheter when the anchor device is in place relative to the catheter insertion site; and
   a pull handle including first and second separable portions, and the pull handle being coupled to the first and second ends of the first suture, the pull handle being configured to selectively tension the first suture;

wherein the first and second separable portions comprise at least first and second pull tabs.

17. A catheter anchor device, comprising:

an adhesive element configured to be secured to a patient's skin proximate a catheter insertion site;

a stationary base secured to the adhesive element;

a rotatable ring coupled to the stationary base such that the rotatable ring can be rotated by a user relative to the stationary base;

a first suture coupled to the rotatable ring, the first suture including a loop portion and first and second ends, the loop portion extending about a catheter when the anchor device is in place relative to the catheter insertion site; and a pull handle including first and second separable portions, and the pull handle being coupled to the first and second ends of the first suture, the pull handle being configured to selectively tension the first suture;

wherein each pull tab has at least one aperture defined therein sized to accommodate at least a portion of a finger of a user.

* * * * *